(12) United States Patent
Sohn et al.

(10) Patent No.: US 8,673,822 B2
(45) Date of Patent: Mar. 18, 2014

(54) RAPID SCREENING METHOD OF TRANSLATIONAL FUSION PARTNERS FOR PRODUCING RECOMBINANT PROTEINS AND TRANSLATIONAL FUSION PARTNERS SCREENED THEREFROM

(75) Inventors: Jung-Hoon Sohn, Daejeon (KR); Eui-Sung Choi, Daejeon (KR); Jung-Hoon Bae, Daejeon (KR); Eung-Suck Lee, Seoul (KR); Mi-Kyung Shin, Daejeon (KR)

(73) Assignee: Korea Research Institute of Bioscience and Biotechnology (KR)

( * ) Notice: Subject to any disclaimer, the term of this patent is extended or adjusted under 35 U.S.C. 154(b) by 1707 days.

(21) Appl. No.: 10/586,045

(22) PCT Filed: Dec. 30, 2004

(86) PCT No.: PCT/KR2004/003517
§ 371 (c)(1),
(2), (4) Date: Jun. 12, 2007

(87) PCT Pub. No.: WO2005/068658
PCT Pub. Date: Jul. 28, 2005

(65) Prior Publication Data
US 2007/0275385 A1 Nov. 29, 2007

(30) Foreign Application Priority Data

Jan. 17, 2004 (KR) .................. 10-2004-0003610
Jan. 19, 2004 (KR) .................. 10-2004-0003957

(51) Int. Cl.
*C40B 20/04* (2006.01)
*C40B 30/06* (2006.01)
*C40B 50/06* (2006.01)

(52) U.S. Cl.
USPC .................. 506/4; 506/10; 506/26

(58) Field of Classification Search
USPC .................. 506/4, 10, 26
See application file for complete search history.

(56) References Cited

U.S. PATENT DOCUMENTS

| | | | |
|---|---|---|---|
| 5,037,760 A | 8/1991 | Smith et al. | |
| 5,212,058 A * | 5/1993 | Baker et al. | 435/252.33 |
| 5,362,644 A * | 11/1994 | Boquet et al. | 435/252.3 |
| 5,536,637 A * | 7/1996 | Jacobs | 435/6 |
| 5,547,871 A * | 8/1996 | Black et al. | 435/348 |
| 5,563,046 A * | 10/1996 | Mascarenhas et al. | 435/69.52 |
| 5,712,113 A * | 1/1998 | Chung et al. | 435/69.1 |
| 5,952,171 A | 9/1999 | McCarthy et al. | |
| 6,136,569 A * | 10/2000 | Baker et al. | 435/91.41 |
| 6,150,098 A | 11/2000 | Zhang et al. | |
| 6,228,590 B1 | 5/2001 | Baker | |
| 6,548,633 B1 | 4/2003 | Edwards et al. | |
| 7,029,842 B2 | 4/2006 | Duffner et al. | |
| 2002/0127557 A1 | 9/2002 | Tan et al. | |
| 2004/0110939 A1 | 6/2004 | Edwards et al. | |
| 2009/0181425 A1 | 7/2009 | Sohn et al. | |
| 2010/0159465 A1 | 6/2010 | Sohn et al. | |

FOREIGN PATENT DOCUMENTS

| | | | | |
|---|---|---|---|---|
| EP | 1 170 366 A1 | 1/2002 | | |
| EP | 0 773 296 B1 | 9/2006 | | |
| WO | WO 84/04330 | 11/1984 | | |
| WO | 99/49028 | * 9/1999 | | C12N 15/10 |
| WO | WO 99/49028 A1 | 9/1999 | | |
| WO | WO 01/77315 A1 | 10/2001 | | |
| WO | WO 02/072821 A2 | 9/2002 | | |

OTHER PUBLICATIONS

Baldari, C., et al., "Differential stability of human interleukin 1 beta fragments expressed in yeast," *Protein Eng.* 1:433-437, JRL Press Limited (1987).

Broekhuijsen, M.P., et al., "Secretion of heterologous proteins by *Aspergillus niger*: Production of active human interleukin-6 in a protease-deficient mutant by KEX2-like processing of a glucoamylase-hIL6 fusion protein," *J Biotechnol.* 31:135-145, Elsevier Science Publishers B.V. (Nov. 1993).

Contreras, R., et al., "Efficient KEX2-like Processing of a Glucoamylase-Interleukin-6 Fusion Protein by *Aspergillus nidulans* and Secretion of Mature Interleukin-6," *Bio/Technology (N.Y.)* 9:378-381, Nature Pub. Co. (Apr. 1991).

Crosier, P.S., et al., "In Situ Hybridization Screen in Zebrafish for the Selection of Genes Encoding Secreted Proteins," *Developmental Dynamics* 222:637-644, Wiley-Liss, Inc. (2001).

Dorner, A.J., et al., "Overexpression of GRP78 mitigates stress induction of glucose regulated proteins and blocks secretion of selective proteins in Chinese hamster ovary cells," *The EMBO Journal* 11:1563-1571, Oxford University Press (1992).

Dorner, A.J., et al., "Reduction of Endogenous GRP78 Levels Improves Secretion of a Heterologous Protein in CHO Cells," *Molecular and Cellular Biology* 8:4063-4070, American Society for Microbiology (1988).

Downing, K.J., et al., *Staphylococcus aureus* nuclease is a useful secretion reporter for mycobacteria, *Gene* 239:293-299, Elscience Science B.V. (1999).

Eckart, M.R. and Bussineau, C.M., "Quality and authenticity of heterologous proteins synthesized in yeast," *Curr Opin Biotechnol.* 7:525-530, Current Biology Ltd. (Oct. 1996).

Ferguson, D.A., et al., "Selective Identification of Secreted and Transmembrane Breast Cancer Markers using *Escherichia coli* Ampicillin Secretion Trap," *Cancer Res* 65:8209-8217, American Association for Cancer Research (2005).

Galliciotti, G., et al., "Signal-sequence Trap in Mammalian and Yeast Cells: A Comparison," *J. Membrane Biol.* 183:175-182, Springer-Verlag (2001).

Goo, J.H., et al., "Selection of *Arabidopsis* genes encoding secreted and plasma membrane proteins," *Plant Molecular Biology* 41:415-423, Kluwer Academic Publishers (1999).

Gouka, R.J., et al., "Efficient production of secreted proteins by *Aspergillus*: progress, limitations and prospects," *Appl Microbiol Biotechnol.* 47:1-11, Springer-Verlag (Jan. 1997).

(Continued)

*Primary Examiner* — Amber D Steele
(74) *Attorney, Agent, or Firm* — Sterne, Kessler, Goldstein & Fox P.L.L.C.

(57) ABSTRACT

Disclosed are a method for rapid screening suitable translational fusion partners (TFPs) capable of inducing expression or secretory production of non-producible proteins, which are difficult to produce in conventional recombinant production methods, from a variety of genetic sources, and protein secretion-inducing TFPs obtained using the method.

20 Claims, 14 Drawing Sheets

(56) References Cited

OTHER PUBLICATIONS

Harmsen, M.M., et al., "Overexpression of binding protein and disruption of the *PMR1* gene synergistically stimulate secretion of bovine prochymosin but not plant Thaumatin in yeast," *Appl Microbiol Biotechnol.* 46:365-370, (Nov. 1996).

Hayano, T., et al., "Protein disulfide isomerase mutant lacking its isomerase activity accelerates protein folding in the cell," *FEBS Lett.* 377:505-511, Federation of European Biochemical Societies (Dec. 1995).

Hsu, T.-A., et al., "Effects of Co-expressing Chaperone BiP on Functional Antibody Production in the Baculovirus System," *Protein Expr Purif.* 5:595-603, Academic press, Inc. (Dec. 1994).

Jacobs, K.A., et al., "A genetic selection for isolating cDNAs encoding secreted proteins," *Gene* 198:289-296, Elsevier Science B.V. (1997).

Jeenes, D.J., et al., "A truncated glucoamylase gene fusion for heterologous protein secretion from *Aspergillus niger*," *FEMS Microbiol Lett.* 107:267-272, Federation of European Microbiological Societies (Mar. 1993).

Kjeldsen, T., et al., "Prepro-Leaders Lacking N-linked Glycosylation for Secretory Expression in the Yeast *Saccharomyces cerevisiae*," *Protein Expr Purif.* 14:309-316, Academic Press (Dec. 1998).

Kjeldsen, T., et al., "Synthetic Leaders with Potential BiP Binding Mediate High-Yield Secretion of Correctly Folded Insulin Precursors from *Saccharomyces cerevisiae*," *Protein Expr Purif.* 9:331-336, Academic Press (Apr. 1997).

Klein, R.D., et al., "Selection for genes encoding secreted proteins and receptors," *Proc. Natl. Acad. Sci. USA* 93:7108-7113, National Academy of Sciences (Jul. 1996).

Lee, J., et al., "Novel Secretion System of a Recombinant *Saccharomyces cerevisiae* Using an N-terminus Residue of Human IL-1β as Secretion Enhancer," *Biotechnol. Prog.* 15:884-890, American Chemical Society and American Institute of Chemical Engineers (1999).

Lim, E.M., et al., "Identification of *Mycobacterium tuberculosis* DNA Sequences Encoding Exported Proteins by Using *phoA* Gene Fusions," *J. Bacteriol.* 177:59-65, American Society for Microbiology (Jan. 1995).

MacConaill, L.E., et al., Investigation of Protein Export in *Bifidobacterium breve* UCC2003, *Appl. Environ. Microbiol.* 69:6994-7001, American Society for Microbiology (Dec. 2003).

Makrides, S.C., "Strategies for Achieving High-Level Expression of Genes in *Escherichia coli*," Microbiological Reviews 60:512-538, American Society for Microbiology (1996).

Monteoliva, L., et al., "Large-Scale Identification of Putative Exported Proteins in *Candida albicans* by Genetic Selection," *Eukaryotic Cell* 1:514-525, American Society for Microbiology (Aug. 2002).

Muesch, A., et al., "A novel pathway for secretory proteins?" *TIBS* 15:86-88, Elsevier Science Publishers Ltd. (UK)(Mar. 1990).

Roberts, I.N., et al., "Heterologous gene expression in *Aspergillus niger*: a glucoamylase-porcine pancreatic prophospholipase $A_2$ fusion protein is secreted and processed to yield mature enzyme," *Gene* 122:155-161, Elsevier Science Publishers B.V. (Dec. 1992).

Robinson, A.S., et al., "Protein Disulfide Isomerase Overexpression Increases Secretion of Foreign Proteins in *Saccharomyces cerevisiae*," *Bio/Technology (NY)* 12:381-384, Nature Pub. Co. (Apr. 1994).

Robinson, A.S., et al., "Reduction of BiP Levels Decreases Heterologous Protein Secretion in *Saccharomyces cerevisiae*," *J. Biol. Chem.* 271:10017-10022, American Society for Biochemistry and Molecular Biology (1996).

Sagt, C.M.J., et al., "Introduction of an N-Glycosylation Site Increases Secretion of Heterologous Proteins in Yeasts," *Applied and Environmental Microbiology* 66:4940-4944, American Society for Microbiology (2000).

Schultz, L.D., et al., "Using Molecular Genetics to Improve the Production of Recombinant Proteins by the Yeast *Saccharomyces cerevisiae*," *Ann NY Acad Sci.* 721:148-157, New York Academy of Sciences (May 1994).

Surpili, M.J., et al., "A yeast-based model system for cloning secreted and membrane proteins," *An Acad Bras Cienc* 74:599-608, Academia Brasileira De Ciencias (2002).

Takahashi, S., et al., "Function of the prosequence for in vivo folding and secretion of active *Rhizopus oryzae* lipase in *Saccharomyces cerevisiae*," *Appl Microbiol Biotechnol.* 55:454-462, Springer Verlag (May 2001).

Tan, N.S., et al., "Engineering a novel secretion signal for cross-host recombinant protein expression," *Protein Eng.* 15:337-345, Oxford University Press (2002).

Wang, H. and Ward, M., "Molecular characterization of a PDI-related gene *prpA* in *Aspergillus niger* var. *awamori*," *Curr Genet* 37:57-64, Springer-Verlag (Jan. 2000).

Ward, P.P., et al., "A system for production of commercial quantities of human lactoferrin: a broad spectrum natural antibiotic," *Bio/Technology (NY)*. 13:498-503, (May 1995).

Ward, M., et al., "Improved Production of Chymosin in *Aspergillus* by Expression as a Glucoamylase-Chymosin Fusion," *Bio/Technology* 8:435-440, Nature Pub. Co. (1990).

Preliminary Amendment (unpublished) of Co-pending U.S. Appl. No. 11/914,437 (U.S. Nat'l Phase of PCT/IB2006/003102), Int'l Filing Date: Jul. 13, 2006, Sohn et al.

International Search Report for International Appl. No. PCT/KR2004/003517, Korean Intellectual Property Office, mailed Apr. 7, 2005, see note in Office action.

International Search Report for International Appl. No. PCT/IB2006/003102, Korean Intellectual Property Office, mailed Mar. 30, 2003, see note in Office action.

Lüthi, U., et al., "Human β-secretase activity in yeast detected by a novel cellular growth selection system," *Biochimica et Biophysica Acta* 1620: 167-178, Elsevier Science B.V., NL (2003).

NCBI Entrez, GenBank Report, Accession No. NC_001133, Goffeau, A., et al., Entry Date Dec. 7, 2002.

Ecker, M., et al., "*O*-Mannosylation precedes and potentially controls the *N*-glycosylation of a yeast cell wall glycoprotein," *EMBO Reports*, 4-6: 628-632, Nature Publishing Group, London, GB (2003).

Galliciotti, G., et al., "Signal-sequence trap in mammalian and yeast cells: a comparison," *Journal of Membrane Biology*, 183-3: 175-182, Springer-Vertag, New York (2001).

Tan, N.S., et al., "Engineering a novel secretion signal for cross-host recombinant protein expression," *Protein Engineering*, 15-4: 337-345, Oxford University Press, Surrey, GB (2002).

UniProt Database, "Covalently-linked cell wall protein 11 precursor (CIS3 protein) (Soluble cell wall protein 8)," Accession No. P47001, Obermaier, B., et al., retrieved from EBI accession No. UniProt:P47001, database accession No. P47001, Oct. 10, 2003, 1 page.

\* cited by examiner

Glycosylated →

Non-
glycosylated →

Sc: *S. cerevisiae* fermentation sup. 10 μl
*P. pastoris* fermentation sup. 200 μl (20 fold conc.)

US 8,673,822 B2

RAPID SCREENING METHOD OF TRANSLATIONAL FUSION PARTNERS FOR PRODUCING RECOMBINANT PROTEINS AND TRANSLATIONAL FUSION PARTNERS SCREENED THEREFROM

REFERENCE TO SEQUENCE LISTING SUBMITTED ELECTRONICALLY VIA EFS-WEB

The content of the electronically submitted sequence listing (Name: Sequence Listing.ST25.txt; Size: 19 kilobytes; and Date of Creation: Jun. 7, 2007) filed Jun. 12, 2007 is incorporated herein by reference in its entirety.

TECHNICAL FIELD

The present invention relates to a technique for rapid screening of suitable translational fusion partners (TFPs) capable of inducing expression or secretory production of non-producible proteins, which are difficult to produce using conventional recombinant production methods, from a variety of genetic sources.

BACKGROUND ART

There is a need to develop high-efficiency protein production systems using recombinant microorganisms to analyze human genome sequence data recently obtained through the Human Genome Project and functions of diverse proteins identified at genome units and to produce protein products important in human medical fields. When an expression system is selected to produce a recombinant protein derived from higher organisms such as humans, a variety of factors should be carefully considered, which include growth characteristics of host cells, protein expression levels, possibility of intracellular and extracellular expression, possibility of posttranslational modification, biological activity of expressed proteins. As representative microbial expression systems, *E. coli* and yeast systems are mainly used. *E. coli* is advantageous because many *E. coli*-based expression systems have been developed and *E. coli* expresses heterologous proteins in high levels. However, *E. coli* has the following drawbacks: the inability to perform posttranslational modification for recombinant production of proteins derived from higher eukaryotes, the difficulty in complete secretion of proteins into the culture medium, the lack of folding ability of proteins possessing many disulfide bonds, and the expression of proteins in insoluble forms such as inclusion bodies (Makrides, Microbial Rev., 1996, 60, 512). In addition, since medically valuable disease-associated proteins among human proteins are mostly glycoproteins or membrane proteins, they need glycosylation and folding into a correct three-dimensional structure through disulfide bonds in order to achieve full activity. Thus, these proteins are impossible to produce in *E. coli* and essentially require eukaryotic expression systems such as yeasts.

Yeast *Saccharomyces cerevisiae* is a eukaryotic microorganism proven to be safe to the human body as a GRAS (Generally Recognized As Safe) organism. *S. cerevisiae* has many advantages including easy gene manipulation, various developed expression systems and easy large-scale culture. The advantages further include that *S. cerevisiae* functions to secrete higher cell-derived proteins such as human proteins into the extracellular space, and performs posttranslational modification of proteins, such as glycosylation. The extracellular secretion can be achieved through the artificial fusion of a target protein with a protein secretory signal, and during the secretion of a protein, protein folding or disulfide bond formation and glycosylation occur, thereby producing a fully biologically active recombinant protein. Also, since a biologically active protein can be obtained directly from the culture medium, *S. cerevisiae*-based protein expression systems do not require cost-inefficient cell disruption or refolding so that they are very economical (Eckart and Bussineau, Curr. Opin. Biotechnol., 1996, 7, 525).

However, despite the many advantages of *S. cerevisiae* mentioned above, the problem of present techniques associated with systems for secreting human proteins using yeast *S. cerevisiae* involves non-uniform protein secretion yield ranging from no production to several grams/liter, depending on the human protein, leading to a great difference of more than several thousands in protein secretion yield, thus making it difficult to predict secretion yield. When a heterologous protein is secreted in several grams/liter, this protein production is considered to be cost-effective. In contrast, for the production of proteins expressed in low levels, especially highly valuable human therapeutic proteins, difficulties often occur in the expression and secretion of the proteins. To solve these problems, much research has been focused on secretory factors involved in protein secretion. For example, many studies have been carried out on chaperons, including a method of overexpressing a secretory factor, BiP (KAR2), which helps fold proteins newly synthesized in the endoplasmic reticulum (ER) (Robinson et al., Biotechnol. prog., 1996, 271, 10017), and a method of overexpressing PDI (protein disulfide isomerase) helping the formation of cysteine bonds (Robinson et al., Bio/Technology, 1994, 12, 381; Schultz et al., Ann. N. Y. Acad. Sci., 1994, 721, 148; Hayano et al., FEBS Lett., 1995, 377, 505). Also, another study has been performed to improve secretion through preparation of a fusion partner inducing secretion and fusion with a well-secreted protein (Gouka et al., Appl. Microbiol. Biotechnol., 1997, 47, 1). To date, these methods have been considered to be very successful in improving the secretion of heterologous proteins. Molecular mechanisms of these fusion techniques have been poorly studied, but these fusion techniques have been experimentally proven to reduce limitations in translational or post-translational steps, including facilitating protein translocation and helping protein folding.

Kjeldsen et al. (Protein Expr. Purif., 1997, 9, 331) enhanced the secretion of insulin by fusing insulin precursor with a synthetic leader prepared based on theoretical consideration in order to achieve effective secretion of insulin or insulin precursor. The synthetic leader has an N-glycosylation site and a BiP recognition site so that it extends the residence of the fusion protein in the ER, leading to correct folding of the insulin precursor. Also, the synthetic leader in which an additional glycosylation site is introduced remarkably increased the secretion of insulin in *Aspergillus niger* and *Saccharomyces cerevisiae* (Kjeldsen et al., Protein Expr. Purif., 1998, 14, 309). Similar results were obtained in *Aspergillus awamori* (Ward et al., Bio/Technology, 1989, 8, 435) and when hydrophobic cutinase is expressed in yeast (Sagt et al., Appl. Environ. Microbiol. 2000, 66, 4940). This high-yield secretion of recombinant proteins results from the introduction of glycosylation sites that increase the solubility of recombinant proteins in the ER and induce correct folding of the proteins.

Well-secreted proteins have been employed as fusion partners. For example, fusion expression with glucoamylase from *Aspergillus awamori* resulted in an increase in secretion yield of the following proteins: bovine prochymosin (Ward et al., Bio/Technology, 1989, 8, 435), porcine pancreatic phospholipase A2 (Roberts et al., Gene, 1992, 122, 155), human interleukin-6 (Contreras et al., Bio/Technology 1991, 9, 378; Broekhuijsen et al., J. Biotechnol., 1993, 31, 135), hen egg-white lysozyme (Jeenes et al., FEMS Microbiol Lett, 1993, 107, 267), and human lactoferrin (Ward et al., Bio/Technology, 1995, 13, 498). Increased secretion yield varied, depending on the protein, in a range of 5 to 1000 times. Also, the use of amino-terminal 24 amino acids of human interleukin-1β as a fusion partner in yeast resulted in an increase in secretion yield of human growth hormone and granulocyte colony-stimulating factor (G-CSF) (Lee et al., Biotechnol. Prog., 1999, 15, 884). Human interleukin-1β is secreted without a particular secretory signal (Muesch et al., Trends Biochem. Sci., 1990, 15, 86), and its recombination production is very effective via secretion in yeast (Baldari et al., Protein Eng., 1987, 1, 433). Also, according to a recent report, a fusion partner originally retained in a protein is essential for correct folding of the protein (Takahashi et al., Appl Microbiol. Biotechnol., 2001, 55, 454). When the mature form of *Rhizopus oryzae* lipase (ROL) fused to the pre-pro-leader sequence of the mating factor alpha from *S. cerevisiae* was expressed in order to express ROL in *S. cerevisiae*, secretion of ROL was not observed. However, when ROL was synthesized together with the prosequence, ROL was properly secreted. These results demonstrate that the prosequence of ROL is essential for the folding of ROL itself.

As described above, through much research, various seretory factors have been developed to induce the secretion of recombinant proteins. However, although the developed secretory factors are effective to increase the secretion level of particular proteins, they cannot be used as a general means for the secretory production of all proteins. Dorner et al. reported that overexpression of BiP in CHO cells rather reduces protein secretion (Dorner et al., EMBO J., 1992, 11, 1563), and decreased BiP expression increases protein secretion (Dorner et al., Mol. cell. Biol., 1988, 8, 4063). In yeast, overexpression of KAR2 (BiP) did not enhance the secretion of plant thaumatin (Harmsen et al., Appl. Microbiol. Biotechnol., 1996, 46, 365). Overexpression of BiP in Baculovirus resulted in an increase in levels of a soluble antibody in cell lysates but did not increase secretion yield of the antibody (Hsu et al., Protein Expr. Purif., 1994, 5, 595). When another secretory factor PDI as a foldase was overexpressed in *Aspergillus niger*, secretion of glucoamylase did not increase (Wang and Ward, Curr. Genet. 2000, 37, 57). Secretion improvement using a protein fusion partner was also reported to have a problem of increasing the secretion efficiency only of particular proteins.

DISCLOSURE OF THE INVENTION

As described above, much research has been focused on the effects of secretory factors, but secretory factors have different effects on secretion level depending on the types of proteins and thus cannot be applied to all proteins. Thus, there is a need for a technique of screening an optimal secretory factor specifically applicable to a target protein for maximal secretion of the target protein. In this regard, the present inventors developed a technique of rapidly screening an optimal secretory fusion partner from a genome unit according to types of recombinant proteins.

Accordingly, the present invention aims to provide a method capable of rapidly screening a suitable translational fusion partner (TFP) capable of strongly inducing production of a protein, which is unable to be produced at large scale and low cost due to its low expression levels in yeasts, from a variety of genetic sources including yeasts, and a translational fusion partner capable of stimulating the secretory production of a non-producible protein using the method.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
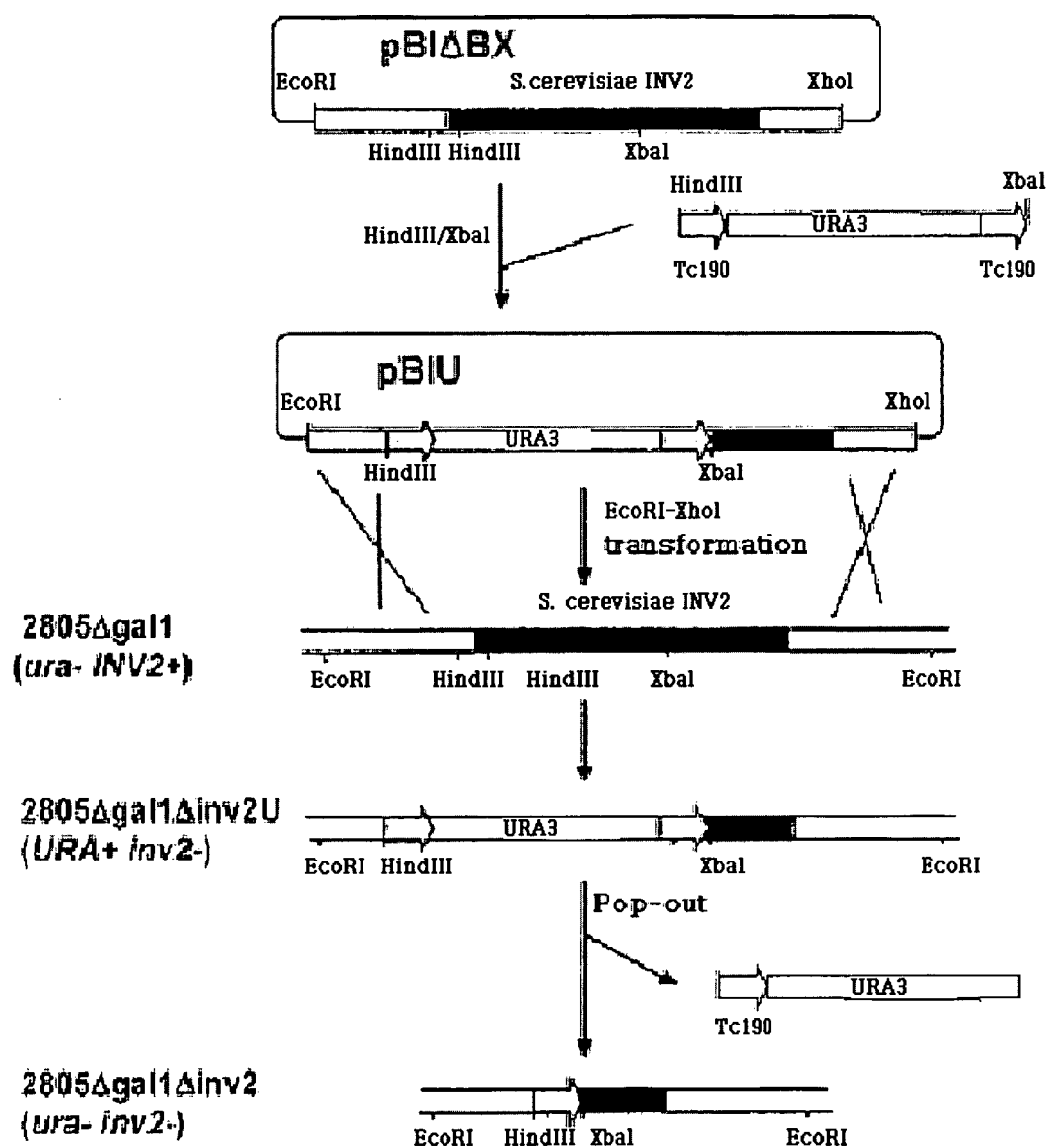
FIG. 1 shows a process of deleting the invertase gene and a pop-out process of a selectable marker.

In one aspect, the present invention relates to a method of screening, from a gene library, a translational fusion partner (TFP) that induces extracellular secretion of a non-producible X-R fusion protein, which is prepared by linking a non-producible target protein gene (X) to a reporter gene (R) for automatic screening, through fusion of the X-R fusion product with other genes.

In one detailed aspect, the present invention relates to a method of screening a suitable translational fusion partner (TFP) for producing a non-producible protein, comprising:

(1) preparing an automatic screening vector including a fusion gene (X-R) in which a gene (X) encoding a non-producible target protein is linked in frame to a reporter gene (R) for automatic screening;

(2) linking a gene library including a TFP inducing secretion of the non-producible fusion protein (X-R) to the automatic screening vector to create a TFP library;

(3) transforming cells having no activity of the reporter gene with the TFP library to detect the activity of a reporter protein; and (4) isolating a gene from transformed cells exerting the activity of the reporter protein and analyzing properties of the TFP.

The term "translational fusion partner (TFP)", as used herein, refers to a gene that is fused to a gene encoding a non-producible protein and induces the secretory production of the non-producible protein. Also, the "translational fusion partner protein" means a protein having an amino acid sequence encoded by the aforementioned TFP gene.

The term "non-producible protein", as used herein, refers to a protein that is difficult to express in host cells, such as *E. coli* or yeasts, due to its native properties with respect to recombinant production of proteins from humans or various organisms. In particular, with respect to the objects of the present invention, a non-producible protein is a protein that is difficult to express in eukaryotic host cells such as yeasts in recombinant production. The screening method of the present invention and the translational fusion partner obtained using the screening method are used for recombinant production of proteins that cannot be recombinantly produced in both prokaryotic cells such as *E. coli* and eukaryotic cells such as yeasts, as well as a plurality of proteins that can be recombinantly produced in prokaryotic cells such as *E. coli* but are cost-ineffective due to their low yield in eukaryotic cells such as yeasts. As used herein, the term "expression" means that a transcriptional and translational product of a gene encoding a particular protein is secreted and obtained as a final desired product.

The reporter gene for automatic screening according to the present invention is selected from, but is not limited to, a gene group encoding proteins capable of being extracellularly secreted, including invertase, sucrase, cellulase, xylanase, maltase, amylase, glucoamylase and galactosidase.

In the screening method, the gene library including a translational fusion partner for inducing the secretion of a non-producible fusion protein may be obtained from a variety of origins, for example, animals, plants and microorganisms, including yeasts or humans. Preferred is a gene library from yeasts. The yeasts for the gene library includes *Candida, Debaryomyces, Hansenula, Kluyveromyces, Pichia, Schizosaccharomyces, Yarrowia, Saccharomyces, Aspergillus, Penicillium, Rhizopus, Trichoderma*, etc. The gene library may be in the form of genomic (chromosomal) DNA or cDNA.

In one embodiment, when a non-producible protein (X), which is difficult to express in recombinant production, is fused to an invertase (I) and expressed in yeast cells, because the secretion of invertase secreted under normal conditions is inhibited by the fused poorly-secreted protein (X), the yeast cells do not grow or their growth is greatly delayed, due to poor expression levels of the fusion protein on a medium containing only sucrose as a carbon source. However, when an effective translational fusion partner capable of inducing the expression and secretion of X-I is introduced, cells rapidly grow on a sucrose medium. Based on this principle, when the X-I fusion protein of a non-producible protein and an invertase is additionally fused to a translational fusion partner library obtained from a variety of origins in the form of TFP-X-I or X-I-TFP, introduced into yeast cells and expressed therein, cells rapidly growing on the sucrose medium are selected, thereby allowing rapid screening of a TFP most suitable for the non-producible protein from a variety of libraries.

Therefore, in a more preferred aspect, the present invention relates to a method of rapidly screening a suitable translational fusion partner (TFP) for producing a non-producible protein, comprising:

(1) preparing a yeast mutant strain deleted for its endogenous invertase gene INV2(I) to develop an automatic screening system using a yeast invertase as a reporter gene;

(2) preparing yeast high-throughput selection (HTS) vectors, pYHTS vectors (pYHTS-F0, pYHTS-F1 or pYHTS-F2) containing a gene (X-I) in which an invertase gene (I) is fused in frame to a non-producible protein gene (X) and which is controlled in expression under a yeast GAL10 promoter;

(3) preparing a translational fusion partner library from yeast genes capable of secreting the fusion gene (X-I) of an invertase and a non-producible protein in the pYHTS vectors;

(4) transforming the library into the yeast mutant strain prepared at step (1) and performing automatic screening on a medium containing only sucrose as a carbon source;

(5) detecting a protein secreted into the medium by culturing yeast cells grown on the sucrose medium; and (6) isolating genes from the yeast cells and analyzing properties of the translational fusion partner.

The present inventors prepared an invertase-deficient yeast mutant and found that invertase can be used as a marker for automatic screening through the expression of a protein fused to the invertase in a yeast strain deleted for its invertase gene. Then, the present inventors prepared vectors for the automatic screening of a translational fusion partner, pYHTS-F0, F1 and F2, using a non-producible protein, human interleukin-2, linking yeast-derived cleaved chromosomal DNA to the vectors to generate a translational fusion partner library, and found, from the TFP library, TFP proteins suitable for the poorly secreted protein human interleukin-2, TFP1, TFP2, TFP3 and TFP4.

Yeast cells need an invertase enzyme encoded by a yeast INV2 gene using only sucrose as a carbon source. As used herein, the term "automatic screening system using invertase" means a system for selecting a yeast strain growing on a sucrose medium according to the expression of an INV2 gene introduced into a vector while the yeast strain is deleted for its chromosomal INV2 gene.

The enzyme invertase has been used as a reporter protein. For example, U.S. Pat. No. 6,228,590 and EP 0 907 727 B1 disclose methods of screening fusion partners inducing the secretion of invertase lacking the native secretory signal sequence and thus not being secreted. In contrast, the present invention employs the invertase enzyme for screening a translational fusion partner capable of inducing the expression of a non-producible fusion protein in which the invertase enzyme is fused to a non-producible protein. As a result, the number of transformants expressing invertase was remarkably reduced, thereby giving better distinguish discrimination between true and false positives. Thus, the present invention allows rapid identification of a translational fusion partner specifically applicable to a non-producible protein.

Translational fusion partners TFP1, TFP2, TFP3 and TFP4 and derivatives thereof, which are obtained in the present invention, may be applied to a variety of proteins produced at commercial large scale. These proteins include, but are not limited to, cytokines (e.g., interleukin), serum proteins (e.g., coagulation factors including Factors VII, VIII and IX), immunoglobulins, cytokine receptors, lactoferrin, interferons (e.g., interferon-$\alpha$, -$\beta$ and -$\gamma$), colony stimulating factors (e.g., GM-CSF, G-CSF), phospholipase activating protein (PLAP), insulin, tumor necrosis factor (TNF), growth factors (e.g., tissue growth factors and epithelial growth factors, such as TGFA or TGFP, epidermal growth factor (EGF), platelet-derived growth factor (PDGF), fibroblast growth factor (FGF)), hormones (e.g., follicle stimulating hormone, thyroid stimulating hormone, antidiuretic hormone, pigmentary hormone and parathyroid hormone, luteinizing hormone-releasing hormone and derivatives thereof), calcitonin, calcitonin gene related peptide (CGPR), enkephalin, somatomedin, erythropoietin, hypothalamic releasing factor, prolactin, chorionic gonadotropin, tissue plasminogen activator, growth hormone releasing peptide (GHPR), thymic humoral factor (THF), and anticancer and antibiotic peptides. Also, these proteins may include enzymes, which are exemplified by carbohydrate-specific enzymes, proteolytic enzymes, lipases, oxidoreductases, transferases, hydrolases, lyases, isomerases and ligases. Concrete examples of enzymes include, but are not limited to, asparaginase, arginase, arginine deaminase, adenosine deaminase, peroxide dismutase, endotoxinase, catalase, chymotrypsin, uricase, adenosine diphosphatase, tyrosinase, and bilirubin oxidase. Examples of the carbohydrate-specific enzymes include glucose oxidase, glucodase, galactosidase, glucocerebrosidase and glucuronidase.

Non-producible protein genes are genes that encode the aforementioned proteins having human medical or industrial importance, the recombinant production of which is required, and are isolated or chemically synthesized from genes derived from a variety of plants, animals and microorganisms, including humans.

The automatic screening vector of the present invention includes a promoter gene, a gene encoding a target protein, which is deleted for translation initiation and termination codons, and a reporter gene fused in frame to the gene encoding the target protein. The promoter gene is preferably selected from the group consisting of GAPDH, PGK, ADH, PHO5, GAL1 and GAL10.

In the automatic screening method of the present invention, the host cells to be transformed include, but are not limited to, yeasts, such as *Candida, Debaryomyces, Hansenula, Kluyveromyces, Pichia, Schizosaccharomyces, Yarrowia* and *Saccharomyces* species, fungi, such as *Aspergillus, Penicillium, Rhizopus* and *Trichoderma* species, and bacteria, such as *Escherichia* and *Bacillus* species.

The rapid screening method of a suitable TFP for producing a non-producible protein according to the present invention is preferably used for producing non-producible proteins that are not expressed or are expressed in low levels. Also, the present method may be used for screening a TFP capable of increasing expression levels of a low-level expressed protein. As in one embodiment of the present invention, when the invertase enzyme is used as a reporter, cells are selected according to their growth rates on the sucrose medium, thereby allowing discrimination of more effective TFPs.

In another aspect, the present invention relates to vectors, pYHTS-F0, F1 and F2, for rapidly screening a suitable fusion partner for stimulating the secretory production of a non-producible protein interleukin-2. These screening vectors include a fusion gene of the non-producible protein human interleukin-2 and invertase, and contain a BamHI recognition site having three different reading frames at an amino terminal end of the interleukin-2 gene.

In an embodiment of the present invention, in order to rapidly screen suitable fusion partners stimulating the secretory production of human interleukin-2 in yeast cells, yeast chromosomal DNA is randomly cleaved and inserted into the three screening vectors (pYHTS-F0, F1 and F2). A yeast strain lacking invertase is transformed with the resulting screening vectors, and colonies growing on a sucrose medium are selected to identify suitable fusion partners capable of secreting the fusion protein of non-producible interleukin-2 and invertase into the culture medium.

Human interleukin-2, which is a highly hydrophobic protein, is difficult to express in yeast cells because the recombinant protein expressed at large scale by a strong promoter is not folded rapidly into an active form in the ER but forms aggregates that may block the function of the ER. Thus, when fused to interleukin-2, invertase is also not secreted, and yeast cells cannot grow on a sucrose medium. Translational fusion partners capable of effectively secreting this fusion protein may be identified by inserting a yeast genomic library upstream of the interleukin-2 gene, transforming the library into a yeast strain and selecting transformants growing on a sucrose medium.

In an embodiment, in order to obtain fusion partners inducing secretion of the non-producible protein interleukin-2, the present inventors isolated genes from transformants growing on a sucrose medium, re-transformed the genes into *E. coli*, and recovered four different plasmids (pYHTS-TFP1, TFP2, TFP3 and TFP4). Four different translational fusion partner genes carried in the plasmids, TFP1 (SEQ ID NO. 2), TFP2 (SEQ ID NO. 4), TFP3 (SEQ ID NO. 6) and TFP4 (SEQ ID NO. 8), were obtained, and corresponding amino acid sequences are represented by SEQ ID NOS. 1, 3, 5 and 7, respectively.

The invertase gene was deleted in the obtained vectors pYHTS-TFP1, TFP2, TFP3 and TFP4, and a translation termination codon was inserted into the interleukin-2 gene, thus generating pYIL-TFP1, TFP2, TFP3 and TFP4. Since these vectors secrete interleukin-2 in the form of being fused to a translational fusion partner, a recognition site for Kex2p proteinase is inserted to allow automatic removal of the translational fusion partner, thus generating pYIL-KRTFP1, KRTFP2, KRTFP3 and KRTFP4. Also, human granulocyte colony stimulating factor (G-CSF) is fused to the translational fusion partners TFP1 to TFP4, thus generating vectors pYGCSF-TFP1 to pYGCSF-TFP4, respectively. These vectors demonstrated that the TFPs are effective in secretory production of proteins other than human interleukin-2.

On the other hand, when a conventional expression-secretion system (AMY, amylase secretory signal) is used for large-scale secretory production in a recombinant yeast strain, a CalB14 mutant having about 6-fold improved specific activity through molecular evolution of wild-type *Candida antarctica* lipase B (CalB) that has attracted much interest due to its potential use in industrial applications, the CalB14 is not effectively secreted at an optimal yeast culture temperature of 30° C. but is secreted at a low temperature of 22° C. Since the conventional system has problems of low growth rates of yeast in large-scale fermentation and high cost for temperature control of a fermentor, especially in the summer, there is a need for a secretion system allowing secretory production at an optimal culture temperature. In the present invention, these problems are solved by preparing a pYGT3-CalB4 vector carrying CalB fused to TFP3.

Thus, in a further aspect, the present invention relates to a translational fusion partner TFP1 protein represented by SEQ ID NO. 1 or an analogue thereof. Also, the present invention relates to a gene encoding a translational fusion partner TFP1 protein represented by SEQ ID NO. 1 or an analogue thereof. The scope of the present invention includes a translational fusion partner TFP1 protein having an amino acid sequence represented by SEQ ID NO. 1 or an amino acid sequence homologous thereto, having preferably 75%, more preferably 85%, even more preferably 90% and most preferably 95% or higher homology. Also, the scope of the present invention includes a gene having a DNA sequence encoding a translational fusion partner TFP1 protein represented by SEQ ID NO. 1, or a DNA sequence homologous thereto, having preferably 75%, more preferably 85%, even more preferably 90% and most preferably 95% or higher homology. Preferably, the gene is a gene of SEQ ID NO. 2. Further, the present invention relates to a recombinant vector comprising the gene. Preferably, the gene carried in the recombinant vector is a gene of SEQ ID NO. 2. Examples of the recombinant vector include pYIL-TFP1, pYIL-KRTFP1, pYGCSF-TFP1, pYGCSF-KRTFP1 and pGAP-TFP1-GCSF. Still further, the present invention relates to a cell transformed with the recombinant vector. *Escherichia coli* transformed with pYIL-KRTFP1 was deposited at KCTC (Korean Collection for Type Cultures) on Nov. 11, 2003, and assigned accession number KCTC 10544BP.

In still another aspect, the present invention relates to a translational fusion partner TFP2 protein represented by SEQ ID NO. 3 or an analogue thereof. Also, the present invention relates to a gene encoding a translational fusion partner TFP2 protein represented by SEQ ID NO. 3 or an analogue thereof. The scope of the present invention includes a translational fusion partner TFP2 protein having an amino acid sequence represented by SEQ ID NO. 3 or an amino acid sequence homologous thereto, having preferably 75%, more preferably 85%, even more preferably 90% and most preferably 95% or higher homology. Also, the scope of the present invention includes a gene having a DNA sequence encoding a translational fusion partner TFP2 protein represented by SEQ ID NO. 3, or a DNA sequence homologous thereto, having preferably 75%, more preferably 85%, even more preferably 90% and most preferably 95% or higher homology. Preferably, the gene is a gene of SEQ ID NO. 4. Further, the present invention relates to a recombinant vector comprising the gene. Preferably, the gene carried in the recombinant vector is a gene of SEQ ID NO. 4. Examples of the recombinant vector include pYIL-TFP2, pYIL-KRTFP2, pYGCSF-TFP2 and pYGCSF-KRTFP2. Still further, the present invention relates to a cell transformed with the recombinant vector. *Escherichia coli* transformed with pYIL-KRTFP2 was deposited at KCTC (Korean Collection for Type Cultures) on Nov. 11, 2003, and assigned accession number KCTC 10545BP.

In still another aspect, the present invention relates to a translational fusion partner TFP3 protein represented by SEQ ID NO. 5 or an analogue thereof. Also, the present invention relates to a gene encoding a translational fusion partner TFP3 protein represented by SEQ ID NO. 5 or an analogue thereof. The scope of the present invention includes a translational fusion partner TFP3 protein having an amino acid sequence represented by SEQ ID NO. 5 or an amino acid sequence homologous thereto, having preferably 75%, more preferably 85%, even more preferably 90% and most preferably 95% or higher homology. Also, the scope of the present invention includes a gene having a DNA sequence encoding a translational fusion partner TFP3 protein represented by SEQ ID NO. 5, or a DNA sequence homologous thereto, having preferably 75%, more preferably 85%, even more preferably 90% and most preferably 95% or higher homology. Preferably, the gene is a gene of SEQ ID NO. 6. Further, the present invention relates to a recombinant vector comprising the gene. Preferably, the gene carried in the recombinant vector is a gene of SEQ ID NO. 6. Examples of the recombinant vector include pYIL-TFP3, pYIL-KRTFP3, pYGCSF-TFP3, pYGCSF-KRTFP3 and pYGT3-CalB14. Still further, the present invention relates to a cell transformed with the recombinant vector. Escherichia coli transformed with pYIL-KRTFP3 was deposited at KCTC (Korean Collection for Type Cultures) on Nov. 11, 2003, and assigned accession number KCTC 10546BP.

In still another aspect, the present invention relates to a translational fusion partner TFP4 protein represented by SEQ ID NO. 7 or an analogue thereof. Also, the present invention relates to a gene encoding a translational fusion partner TFP4 protein represented by SEQ ID NO. 7 or an analogue thereof. The scope of the present invention includes a translational fusion partner TFP4 protein having an amino acid sequence represented by SEQ ID NO. 7 or an amino acid sequence homologous thereto, having preferably 75%, more preferably 85%, even more preferably 90% and most preferably 95% or higher homology. Also, the scope of the present invention includes a gene having a DNA sequence encoding a translational fusion partner TFP4 protein represented by SEQ ID NO. 7, or a DNA sequence homologous thereto, having preferably 75%, more preferably 85%, even more preferably 90% and most preferably 95% or higher homology. Preferably, the gene is a gene of SEQ ID NO. 8. Further, the present invention relates to a recombinant vector comprising the gene. Preferably, the gene carried in the recombinant vector is a gene of SEQ ID NO. 8. Examples of the recombinant vector include pYIL-TFP4, pYIL-KRTFP4, pYGCSF-TFP4 and pYGCSF-KRTFP4. Still further, the present invention relates to a cell transformed with the recombinant vector. Escherichia coli transformed with pYIL-KRTFP4 was deposited at KCTC (Korean Collection for Type Cultures) on Nov. 11, 2003, and assigned accession number KCTC 10547BP.

The term "analogue", as used for a translational fusion partner protein or gene herein, means a functional equivalent that exerts the activity of the translational fusion partner by inducing secretory production of a non-producible protein when a translational fusion partner gene is fused to a gene encoding the non-producible protein. In the case of the TFP protein, the analogue may include, for example, substitutions between amino acids having the same properties (e.g., replacement of a hydrophobic amino acid with another hydrophobic amino acid, replacement of a hydrophilic amino acid with another hydrophilic amino acid, replacement of a basic amino acid with another basic amino acid, replacement of an acidic amino acid with another acidic amino acid), deletions and insertions of amino acids, or combinations thereof.

With respect to substitution analogues of the translational fusion partner proteins of the present invention, amino acid substitutions in proteins and peptides which do not generally alter the activity of the proteins or peptides are known in the art (H. Neurath, R. L. Hill, The Proteins, Academic Press, New York, 1979). The most commonly occurring substitutions are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions.

In addition, with respect to deletion analogues of the translational fusion partner proteins of the present invention, the deletion of a portion of the whole sequence of the translational fusion partner genes identified using a genomic library (chromosomal library) or a cDNA library may not affect, or may stimulate, the secretion of a non-producible protein. The present inventors investigated the effect of deletion analogue fragments of the translational fusion partners TFP1, TFP2, TFP3 and TFP4 on the secretion of a non-producible protein. A vector carrying TFP1 that is deleted in a serine/alanine-rich sequence, an N-glycosylation site or both did not secrete a non-producible protein. In contrast, a vector (pYIL-KRT1-4) carrying TFP1 that has been deleted in the 5'-UTR (5'-untranslated region) increased expression levels of the non-producible protein over three times. Also, when the 3'-end was additionally deleted (pYIL-KRT1-3), the secretion of the non-producible protein was induced. Thus, deletion analogues of the translational fusion partners of the present invention in a 5'-UTR and partially deleted TFPs in 3'-end are included in the scope of the present invention, as long as they do not negatively affect the secretion of a non-producible protein.

In a detailed aspect, the present invention provides a translational fusion partner TFP1-3 protein represented by SEQ ID NO. 9 or an analogue thereof. Also, the present invention provides a gene encoding a translational fusion partner TFP1-3 protein represented by SEQ ID NO. 9 or an analogue thereof. The scope of the present invention includes a translational fusion partner TFP1-3 protein having an amino acid sequence represented by SEQ ID NO. 9 or an amino acid sequence homologous thereto, having preferably 75%, more preferably 85%, even more preferably 90% and most preferably 95% or higher homology. Also, the scope of the present invention includes a gene having a DNA sequence encoding a translational fusion partner TFP1-3 protein represented by SEQ ID NO. 9, or a DNA sequence homologous thereto, having preferably 75%, more preferably 85%, even more preferably 90% and most preferably 95% or higher homology. Further, the present invention provides a recombinant vector comprising the gene. Preferably, the gene carried in the recombinant vector is a gene encoding a translational fusion partner TFP1-3 represented by SEQ ID NO. 9. An illustrative example of the recombinant vector is pYIL-KRT1-3 (also, referred to as pYIL-KRTFP1-3). Still further, the present invention relates to a cell transformed with the recombinant vector. Escherichia coli transformed with pYIL-KRT1-3 was deposited at KCTC (Korean Collection for Type Cultures) on Nov. 11, 2003, and assigned accession number KCTC 10548BP.

In another detailed aspect, the present invention relates to a translational fusion partner TFP1-4 protein encoded by a gene represented by SEQ ID NO. 10 or an analogue thereof. Also, the present invention relates to a gene encoding a translational fusion partner TFP1-4 and represented by SEQ ID NO. 10 or an analogue thereof. The scope of the present invention includes a translational fusion partner TFP1-4 protein having an amino acid sequence encoded by a gene represented by SEQ ID NO. 10 or an amino acid sequence homologous thereto, having preferably 75%, more preferably 85%, even more preferably 90% and most preferably 95% or higher homology. Also, the scope of the present invention includes a gene having a DNA sequence represented by SEQ ID NO. 10, or a DNA sequence homologous thereto, having preferably 75%, more preferably 85%, even more preferably 90% and most preferably 95% or higher homology. The present invention provides a recombinant vector comprising a gene encoding a translational fusion partner TFP1-4 and represented by SEQ ID NO. 10 or an analogue thereof. Also, the present invention provides a recombinant vector comprising a gene having a DNA sequence encoding a translational fusion partner TFP1-4 and represented by SEQ ID NO. 10 or a DNA sequence homologous thereto, having preferably 75%, more preferably 85%, even more preferably 90% and most preferably 95% or higher homology. An illustrative example of the recombinant vector is pYIL-KRT1-4(also, referred to as pYIL-KRTFP1-4). Further, the present invention provides a cell transformed with the recombinant vector. *Escherichia coli* transformed with pYIL-KRT1-4 was deposited at KCTC (Korean Collection for Type Cultures) on Nov. 11, 2003, and assigned accession number KCTC 10549BP.

In addition, with respect to insertion analogues of the translational fusion partner proteins of the present invention, the addition of a certain sequence to the whole sequence or a partial sequence exerting activity of the translational fusion partner genes identified using a genomic library or a cDNA library may not affect, or may stimulate, the secretion of a non-producible protein. The present inventors investigated the effect of insertion analogues of the translational fusion partners on the secretion of a non-producible protein. Two insertion analogues of TFP3 (104 amino acids), TFP3-3 (189 amino acids) and TFP3-4 (222 amino acids), reduced secretion yield. In contrast, TFP3-1 prepared by adding an N-glycosylation site of 26 amino acids to TFP3 increased the secretion of G-CSF about three times compared to TFP3. Also, TFP3-1-1 (134 amino acids), prepared by adding 4 amino acids to TFP3-1, and TFP3-1-2 (143 amino acids), prepared by adding 13 amino acids to TFP3-1, greatly reduced levels of a fusion protein not processed by Kex2p during secretion without a decrease in the secretion yield of G-CSF. Thus, insertion analogues of the translational fusion partners of the present invention, which have additions of a N-glycosylation site and a region allowing the approach of Kex2p proteinase for cleavage of a fusion site, are included in the scope of the present invention, as long as they do not negatively affect the secretion of a non-producible protein.

In a detailed aspect, the present invention provides a translational fusion partner TFP3-1-1 protein represented by SEQ ID NO. 40 or an analogue thereof. Also, the present invention provides a gene encoding a translational fusion partner TFP3-1-1 protein represented by SEQ ID NO. 40 or an analogue thereof. The scope of the present invention includes a translational fusion partner TFP3-1-1 protein having an amino acid sequence represented by SEQ ID NO. 40 or an amino acid sequence homologous thereto, having preferably 75%, more preferably 85%, even more preferably 90% and most preferably 95% or higher homology. Also, the scope of the present invention includes a gene having a DNA sequence encoding a translational fusion partner TFP3-1-1 protein represented by SEQ ID NO. 40, or a DNA sequence homologous thereto, having preferably 75%, more preferably 85%, even more preferably 90% and most preferably 95% or higher homology. Preferably, the gene is a gene of SEQ ID NO. 41. Further, the present invention provides a recombinant vector comprising the gene. Preferably, the gene carried in the recombinant vector is a gene of SEQ ID NO. 41. An illustrative example of the recombinant vector is pYGT3-1-1-GCSF. Still further, the present invention provides a cell transformed with the recombinant vector. *Escherichia coli* transformed with pYGT3-1-1-GCSF was deposited at KCTC (Korean Collection for Type Cultures) on Dec. 21, 2004, and assigned accession number KCTC 10753BP.

In another detailed aspect, the present invention provides a translational fusion partner TFP3-1-2 protein represented by SEQ ID NO. 42 or an analogue thereof. Also, the present invention provides a gene encoding a translational fusion partner TFP3-1-2 protein represented by SEQ ID NO. 42 or an analogue thereof. The scope of the present invention includes a translational fusion partner TFP3-1-2 protein having an amino acid sequence represented by SEQ ID NO. 42 or an amino acid sequence homologous thereto, having preferably 75%, more preferably 85%, even more preferably 90% and most preferably 95% or higher homology. Also, the scope of the present invention includes a gene having a DNA sequence encoding a translational fusion partner TFP3-1-2 protein represented by SEQ ID NO. 42, or a DNA sequence homologous thereto, having preferably 75%, more preferably 85%, even more preferably 90% and most preferably 95% or higher homology. Preferably, the gene is a gene of SEQ ID NO. 43. Further, the present invention provides a recombinant vector comprising the gene. Preferably, the gene carried in the recombinant vector is a gene of SEQ ID NO. 43. An illustrative example of the recombinant vector is pYGT3-1-2-GCSF. Still further, the present invention provides a cell transformed with the recombinant vector. *Escherichia coli* transformed with pYGT3-1-2-GCSF was deposited at KCTC (Korean Collection for Type Cultures) on Dec. 21, 2004, and assigned accession number KCTC 10754BP.

The term "homologous", as used for a translational fusion partner protein or gene herein, is intended to express similarity to the wild-type amino acid sequence and the wild-type nucleotide sequence. In case of the protein, "homologous" includes an amino acid sequence preferably 75% or higher, more preferably 85% or higher, even more preferably 90% or higher and most preferably 95% or higher identical to an amino acid sequence of the TFP protein of the present invention. Typically, protein homologues may include an active site identical to a target protein. In the case of the gene, "homologous" includes a DNA sequence preferably 75% or higher, more preferably 85% or higher, even more preferably 90% or higher and most preferably 95% or higher identical to a DNA sequence encoding the TFP protein of the present invention. The homology evaluation may be done with the naked eye or using a commercially available program. Using a commercially available computer program, the homology between two or more sequences may be expressed as a percentage (%), and the homology (%) between adjacent sequences may be evaluated.

The translational fusion partners identified according to the present invention for the secretory production of non-producible proteins are used in the form of being fused to a gene encoding a non-producible protein and is inserted into a vector for the secretory production of the non-producible protein. The term "vector", as used herein, refers to a DNA construct that contains a DNA sequence operably linked to regulatory sequences capable of controlling the expression of a protein in a suitable host and sequences introduced for facilitating other genetic manipulation or optimizing the expression of the protein. Such regulatory sequences include a promoter for transcription control, an operator selectively added for transcription control, a suitable mRNA ribosome binding site and sequences controlling termination of transcription/translation. Such a vector for insertion of an exogenous gene may be a plasmid, a virus, a cosmid, or the like. The vector includes cloning vectors and expression vectors. The cloning vector is a replicable plasmid into which exogenous DNA is inserted, and delivers exogenous DNA into host cells transformed therewith. The expression vector typically means a carrier into which a fragment of exogenous DNA, generally a fragment of double-stranded DNA, is inserted. "Exogenous DNA" refers to heterogeneous DNA that does not naturally occur in host cells. The expression vector is able to replicate independently of host chromosomal DNA in host cells so that inserted exogenous DNA may be produced. As generally known in the art, in order to increase the expression level of a transfected gene in a host cell, the gene should be operably linked to transcription and translation regulatory sequences functional in a host cell selected as an expression system.

The term "transformation", as used herein with respect to transformation using a recombinant vector containing a translational fusion partner, means introducing DNA into a suitable host cell so that the DNA is replicable, either as an extrachromosomal element, or by chromosomal integration. Host cells useful for the transformation according to the present invention may be prokaryotic or eukaryotic. In addition, host cells having high transformation efficiency of foreign DNA and having high expression levels of an introduced DNA may be typically used. Examples of host cells include prokaryotic and eukaryotic cells such as *Escherichia* sp., *Pseudomonas* sp., *Bacillus* sp., *Steptomyces* sp., fungi and yeast, insect cells such as *Spodoptera frugiperda* (Sf9), and animal cells such as CHO, COS 1, COS 7, BSC 1, BSC 40 and BMT 10. Also, yeasts including *Candida, Debaryomyces, Hansenula, Kluyveromyces, Pichia, Schizosaccharomyces, Yarrowia* and *Saccharomyces* species may be preferably used as host cells for the large-scale production of a non-producible protein according to the present invention.

In still another aspect, the present invention relates to a method of recombinantly producing non-producible proteins using the aforementioned TFP proteins.

The method for the recombinant production of a non-producible protein comprises preparing an expression vector into which a coding gene of the non-producible protein, fused to a gene encoding the TFP protein, is inserted, and culturing a transformant transformed with the recombinant expression vector. In detail, the present invention relates to a method of recombinantly producing a non-producible protein using a protein having an amino acid sequence represented by SEQ ID NO. 1, 3, 5, 7, 9, 40 or 42 or an amino acid sequence homologous thereto, having preferably 75%, more preferably 85%, even more preferably 90% and most preferably 95% or higher homology, or using a protein having an amino acid sequence encoded by a gene represented by SEQ ID NO. 10 or an amino acid sequence homologous thereto, having preferably 75% or higher, more preferably 85% or higher, even more preferably 90% or higher and most preferably 95% or higher homology. Preferably, the protein represented by SEQ ID NO. 1 is encoded by a gene represented by SEQ ID NO. 2, the protein represented by SEQ ID NO. 3 is encoded by a gene represented by SEQ ID NO. 4, the protein represented by SEQ ID NO. 5 is encoded by a gene represented by SEQ ID NO. 6, the protein represented by SEQ ID NO. 7 is encoded by a gene represented by SEQ ID NO. 8, the protein represented by SEQ ID NO. 40 is encoded by a gene represented by SEQ ID NO. 41, and the protein represented by SEQ ID NO. 42 is encoded by a gene represented by SEQ ID NO. 43.

A better understanding of the present invention may be obtained through the following examples which are set forth to illustrate, but are not to be constructed as the limit of the present invention.

EXAMPLE 1

Preparation of Invertase-Deficient Yeast Mutant

For rapid screening of translational fusion partners of non-producible proteins, an automatic screening system was established through the evaluation of cell growth in a sucrose medium using yeast invertase as a reporter.

A yeast strain deficient for invertase activity was required to use the invertase gene contained in a vector as a reporter gene upon screening after transformation. Thus, the INV2 gene was deleted in yeast chromosomal DNA. In order to prepare a cassette for inducing gene deletion, a pRB58 plasmid (Carlson et al., Cell, 1982, 20, 145) was digested with EcoRI and XhoI, and an INV2 coding gene was recovered and introduced into EcoRI/XhoI sites of pBluescript KS+ (Stratagene, USA), thus generating pBIABX. As shown in FIG. 1, an URA3 gene having a repeat sequence of 190 bp (Tc190) at both its ends was inserted into HindIII-XbaI sites of the INV2 gene contained in the pBIABX, thus generating pBIU. The pBIU was digested with both EcoRI and XhoI, and was transformed into *Saccharomyces cerevisiae* Y2805Δgal1 (Mat a ura3 INV2 pep4::HIS3 gal1 can1) strain (S K Rhee, Korea Research Institute of Bioscience and Biotechnology). The transformant, Y2805Δgal1Δinv2U (Mat a inv2::URA3 pep4:: HIS3 gal1 can1), was selected in a selection medium lacking uracil.

Figure 2:
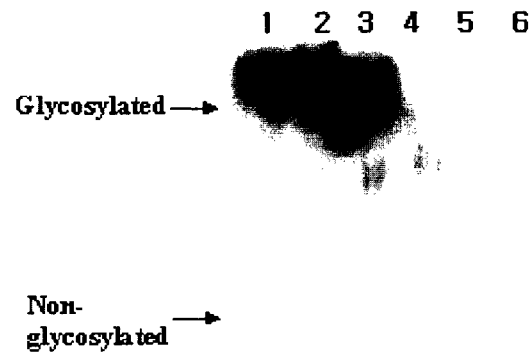
FIG. 2 shows zymogram analysis for invertase activity (lanes 1, 2 and 3: wild-type *Saccharomyces cerevisiae* Y2805; and lanes 4, 5 and 6: invertase-deficient strain (*S. cerevisiae* Y2805Δinv2)
Figure 3:
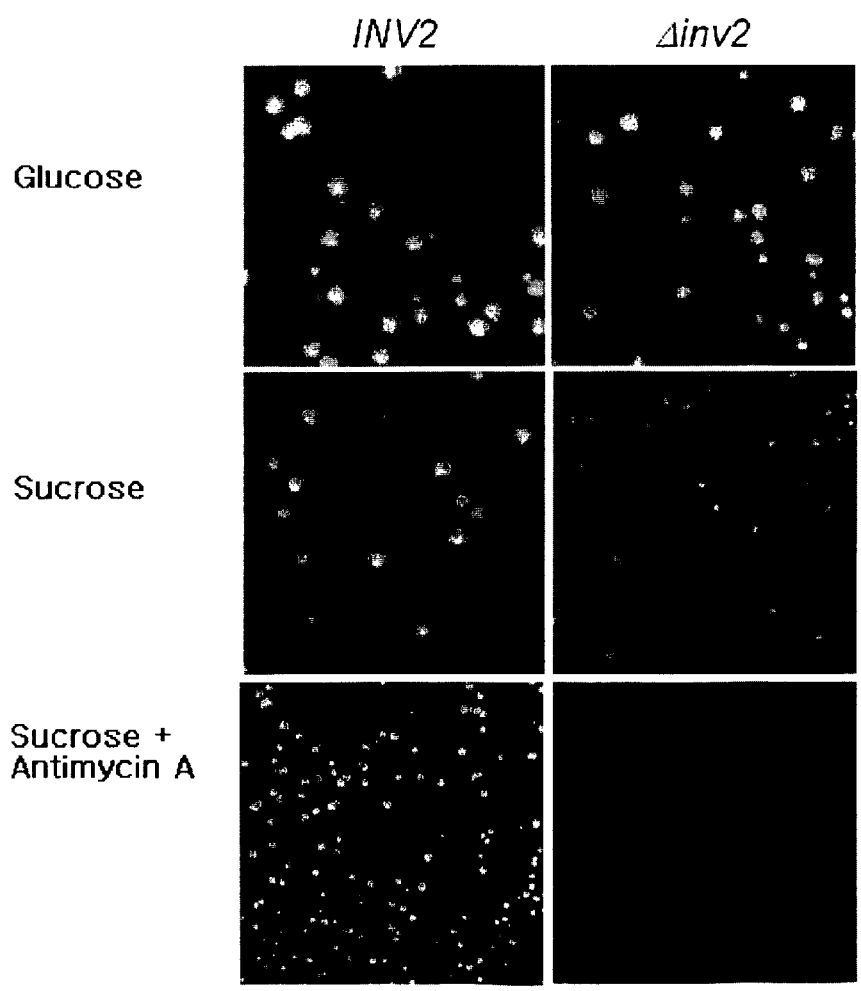
FIG. 3 photographically shows the growth of yeast cells according to carbon sources (1NV2: wild-type *S. cerevisiae* Y2805; and Δinv2: invertase-deficient strain (*S. cerevisiae* Y2805Δinv2)

The selected transformed cells were evaluated to determine whether they completely lost invertase activity. Single colonies were cultured in two media containing glucose and sucrose, respectively, as the sole carbon source. As a result, the colonies grew normally in the glucose medium, but grew very slowly in the sucrose medium compared to a control. In order to investigate the amount of invertase secreted into the culture medium, INV2+ strain and Δinv2 strain were cultured. Proteins contained in the culture supernatants were separated on SDS-PAGE, and the gel was incubated in a sucrose solution for 30 min and subjected to zymogram analysis using a dye, TTC (2,3,5-triphenyl-tetrazolium chloride). As shown in FIG. 2, the Δinv2 strain was found to lose most of its invertase activity. However, the mutant strain had a problem of growing even at very slow rates in the sucrose medium. This is believed to be because cells partially grow by gluconeogenesis through the function of mitochondria. Thus, to solve this problem, antimycin A, an inhibitor of mitochondrial electron transport, was added to the medium to block cell growth. As a result, the growth of the mutant strain was completely inhibited in the presence of antimycin A (FIG. 3).

Figure 4:
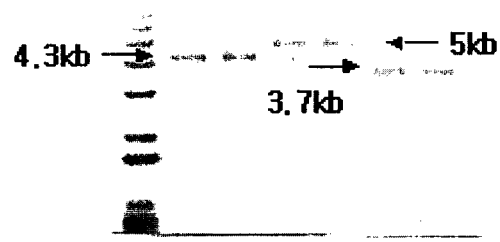
FIG. 4 shows the results of Southern blotting for the deletion of the invertase gene (laens 1 and 2: *S. cerevisiae* Y2805 ura3 INV2; lanes 3 and 4: *S. cerevisiae* Y2805Δinv2U (URA3Δinv2); and lanes 5 and 6: *S. cerevisiae* Y2805Δinv2 (ura3Δinv2)

In order to re-transform the selected strain, Y2805Δgal1Δinv2U (Mat a inv2::URA3 pep4::HIS3 gal1 can1), with a URA3 vector containing a TFP library, it was necessary to remove the URA3 gene used for the deletion of the TNV2 gene. To do this, cells were cultured in a medium containing 5-fluoroorotic acid (5-FOA) and selected for loss of the URA3 gene, thus obtaining a URA3 pop-out deletion strain, Y28058Δgal1Δinv2(Mat a ura3 inv2::Tc190 pep4: :HIS3 gal1 can1) (FIG. 1). Southern blotting was carried out to confirm the deletion of the INV2 gene on chromosome, as expected, and the pop-out of the URA3 gene (FIG. 4). When chromosomal DNA from *S. cerevisiae* Y2805 was treated with EcoRI and analyzed by Southern blotting using an INV2 gene as a probe, a fragment of about 4.3 kb was detected. This size increased to about 5.0 kb when a URA3 gene was inserted (Y2805Δgal1Δinv2U), and decreased to about 3.7 kb when the URA3 gene was popped-out (Y28058gal1Δinv2). As shown in FIG. 4, as expected, the INV2 gene was obviously deleted, and the URA3 gene was lost (pop-out).

EXAMPLE 2

Identification of Automatic Screening System Through Fusion with Invertase

The invertase gene-deficient strain was evaluated for the possibility of being automatically screened in a sucrose medium through the expression of a protein fused to invertase, using a human protein expressed in high levels in yeast, human serum albumin (HSA), and a non-producible protein, human interleukin-2 (IL-2).

First, a pGHSA-INV2 vector in which albumin is fused to invertase was prepared as follows. In order to insert a SfiI recognition sequence into both ends of the HSA gene, PCR was carried out using a sense primer and an anti-sense primer, each of which has a SfiI recognition sequence, JH97 (Sfi-HSA-forward primer) (SEQ ID NO. 11) and JH119 (Sfi-HSA-reverse primer) (SEQ ID NO. 12), respectively, pYHSA5 (Kang et al., J. Microbiol. Biotechnol., 1998, 8, 42) as a template, and Pfu polymerase (Stratagene, USA). PCR conditions included one cycle of 94° C. for 5 min, and 25 cycles of 94° C. for 30 sec, 55° C. for 30 sec and 72° C. for 2 min, followed by one final cycle of 72° C. for 7 min. A PCR product of about 1.8 kb, which was an albumin gene, was obtained. Separately, the invertase gene was amplified by PCR using a set of primers, JH99 (Sfi-INV-forward) (SEQ ID NO. 13) and JH100 (SalI-INV-reverse primer) (SEQ ID NO. 14), and pRB58 as a template under the same conditions. The amplified invertase gene was treated with SfiI/SalI, and was inserted along with the albumin gene treated with PstI/SfiI into PstI/SalI-digested pBluescript (Stratagene, USA). Then, pYHSA5 was digested with SacI/PstI to excise a fragment containing a GAL promoter and a portion of the albumin gene. This fragment, and a PstI-SalI insert excised from the plasmid prepared above, containing a portion of the albumin gene and the invertase gene, were co-ligated into the SacI/SalI sites of a YEGα-HIR525 vector (Choi et al., Appl Microbiol Biotechnol., 1994, 42, 587), thereby generating pGHSA-INV2.

A fusion expression vector of IL-2 and invertase was prepared as follows. The IL-2 gene was amplified by PCR using a set of primers, JH106 (Sfi-IL2-forward primer) (SEQ ID NO. 15) and JH107 (Sfi-IL2-reverse primer) (SEQ ID NO. 16), and pT7-hIL-2 (J K Jung, Korea Research Institute of Bioscience and Biotechnology) as a template. The amplified interleukin gene was inserted into the EcoRV site of pBluescript (Stratagene, USA), thus generating pBKS-IL2. The linearized form of the pBKS-IL2 through SfiI digestion and a SacI-SfiI insert excised from the pGHSA-INV2, containing a GAL promoter and an INV secretory signal, were co-ligated into the SacI/SfiI sites of the pGHSA-INV2, thus generating pGIL2-INV2.

Figure 5:
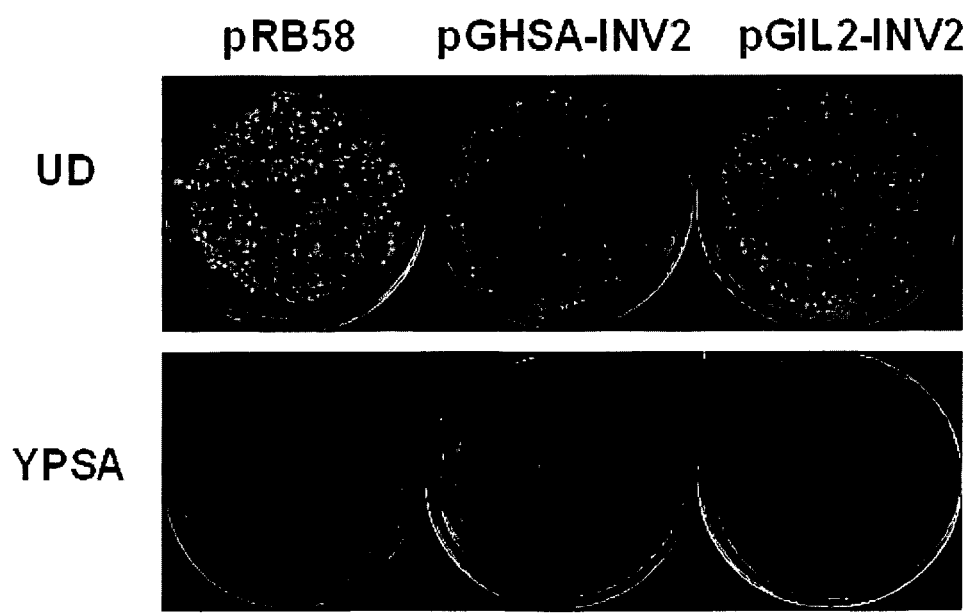
FIG. 5 photographically shows the growth of yeast cells on glucose and sucrose media.

The pGHSA-INV2 vector expressing a fusion protein of albumin and invertase, the pGIL2-INV2 expressing a fusion protein of IL-2 and invertase, and the pRB58 expressing only invertase were individually transformed into a yeast strain (Y2805Δinv2), which is deleted for its endogenous invertase gene and thus unable to grow in a sucrose medium. The transformed cells were smeared onto a medium (UD) containing glucose as a carbon source and a medium (YPSA) containing sucrose as a carbon source, and their growth was observed (FIG. 5). When cells were transformed with the pRB58 vector normally expressing invertase, they normally grew in both carbon sources. Also, when cells were transformed with the pGHSA-INV2 vector in which invertase is fused to albumin leading to the high-level expression of the invertase, they grew well using both carbon sources. In contrast, when cells were transformed with the pGIL2-INV2 vector in which invertase is fused to IL-2 leading to the poor expression of the invertase, they grew normally on the glucose medium but rarely grew on the sucrose medium. This inability of the pGIL2-INV2-transformed cells to grow in the sucrose medium was believed to result from IL-2 being unable to be secreted from the cells and leads to block the secretion of invertase fused thereto. These results indicate that the use of an exogenous invertase gene, introduced into a yeast mutant (Y2805Δinv2), which cannot grow on a sucrose medium due to deletion of its endogenous invertase gene, and secreted or not therein makes automatic screening of yeast cells possible.

EXAMPLE 3

Preparation of Translational Fusion Partner Screening Vector using a Non-Producible Protein Human IL-2

Figure 6:
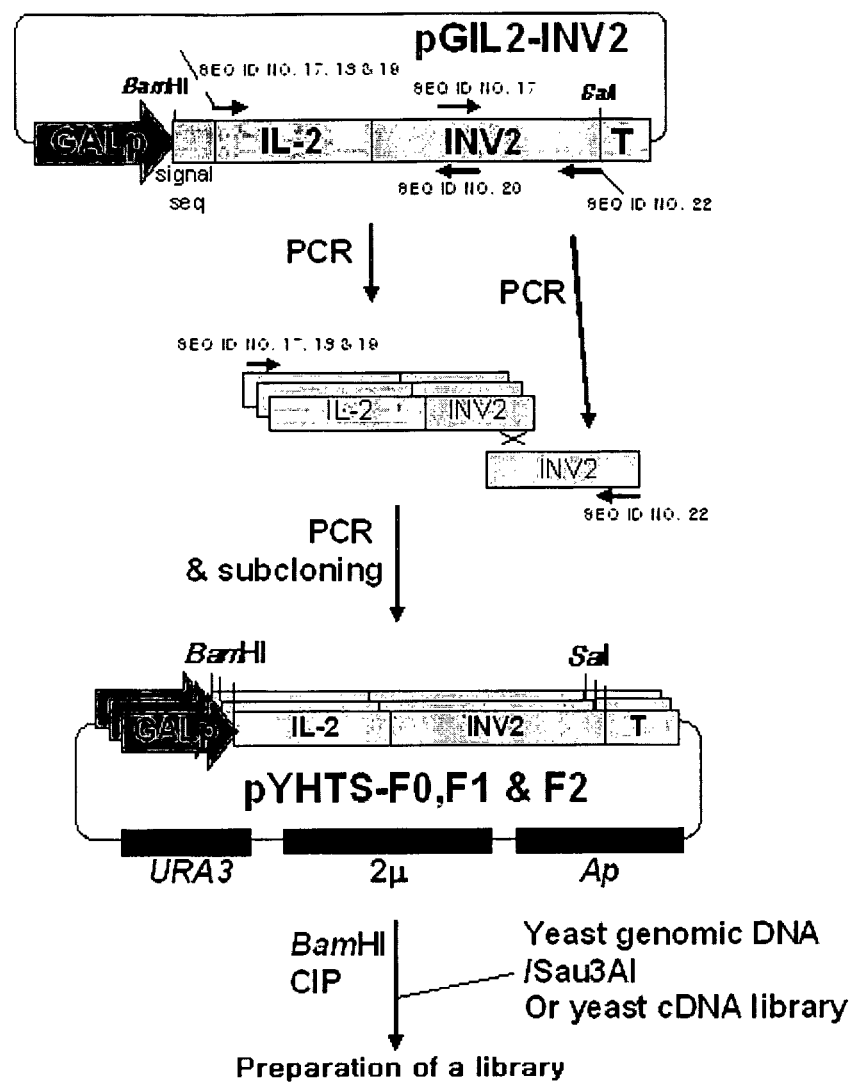
FIG. 6 shows a process of preparing pYHTS-F0, F1 and F2 plasmids and a process of preparing a yeast gene library.

In order to obtain suitable translational fusion partners capable of inducing secretion of a fusion protein using the pGIL2-INV2 vector in which IL-2 is fused to invertase, vectors having three reading frames for preparing a library, pYHTS-F0, F1 and F2, were prepared (FIG. 6).

PCR was carried out using sense primers having three reading frames and a BamHI recognition site, JH120 (BamHI-IL2-1-forward primer) (SEQ ID NO. 17), JH121 (BamHI-IL2-2-forward primer) (SEQ ID NO. 18) and JH122 (BamHI-IL2-3-forward primer) (SEQ ID NO. 19), an antisense primer, JH123 (INV-1-reverse primer) (SEQ ID NO. 20), pGIL2-INV2 as a template, and Pfu polymerase (Stratagene, USA). PCR conditions included one cycle of 94° C. for 3 min, and 25 cycles of 94° C. for 30 sec, 55° C. for 30 sec and 72° C. for 1 min, followed by one final cycle of 72° C. for 7 min. PCR products of about 1.2 kb, containing the IL-2 gene and a portion of the invertase gene, were obtained. Separately, PCR was carried out using a set of primers, JH124 (INV-forward primer) (SEQ ID NO. 21) and JH95 (INV-2-reverse primer) (SEQ ID NO. 22), and pGIL2-INV2 as a template under the same conditions, thus obtaining a fragment of about 0.9 kb containing a portion of the invertase gene. The PCR products were purified from agarose gels. After each of the three 1.2 kb fragments having three reading frames and the 0.9 kb fragment were mixed, secondary PCR was carried out using sense primers, JH120 (SEQ ID NO. 17), JH121 (SEQ ID NO. 18) 및 JH122 (SEQ ID NO. 19), and an antisense primer, JH95 (SEQ ID NO. 22). Three fragments of about 2.1 kb were obtained by agarose electrophoresis. The three recovered 2.1 kb fragments were digested with both BamHI and SalI and individually inserted into pGIL2-INV2 digested with both BamHI and SalI, thus generating pYHTS-F0, F1 and F2.

EXAMPLE 4

Preparation of Suitable Translational Fusion Partner Library from Yeast Genome

A translational fusion partner library was prepared using chromosomal DNA from yeast *Saccharomyces cerevisiae* Y2805 (S K Rhee, Korea Research Institute of Bioscience and Biotechnology) and yeast Hansenula polymorpha DL-1 (ATCC26012). After each chromosomal DNA was partially digested with Sau3AI, DNA fragments ranging from 0.5 kb to 1.0 kb were purified from agarose gels, and ligated with a mixture of pYHTS-F0, F1 and F2 vectors digested with BamHI and treated with calf intestine phosphatase (FIG. 6). Then, *E. coli* DH5α was transformed with the ligated DNA, smeared onto ampicillin-containing LB medium (1% Bactotryptone, 0.5% yeast extract, 1% NaCl), and incubated at 37° for one day. Using the library DNA prepared from the yeast chromosomal DNA, a library of about $5 \times 10^4$ transformants was obtained. All transformants were recovered using sterile distilled water, and library DNA was isolated from the recovered transformants using a plasmid extraction kit (Bioneer, Korea).

EXAMPLE 5

Automatic Screening of Translational Fusion Partners Suitable for a Non-Producible Protein Human IL-2

The library DNA prepared in Example 4 was transformed into yeast *Saccharomyces cerevisiae* Y2805Δgall Δinv2 (Mat a ura3 inv2::Tc190 pep4::HIS3 gall can1) using a lithium acetate procedure (Hills et al., Nucleic Acids Res. 1991, 19, 5791). Then, the transformed cells were smeared onto UD minimal medium lacking uracil (0.67% yeast nitrogen base without amino acids, mixture of various amino acids of proper concentrations, 2% glucose), and YPGSA medium (1% yeast extract, 2% peptone, 2% sucrose, 0.3% galactose, 1 μg/ml antimycin A), and were incubated at 30° C. for 5 days. The number of colonies that emerged on each of the media is given in Table 1, below, in which the number of transformants is compared before and after introduction of translational fusion partners. When yeast cells were transformed with only the vectors (pYHTS-F0, F1 and F2) used for library preparation, about $1\times10^4$ colonies were formed on the glucose medium, but the cells did not grow on the sucrose medium as expected. In contrast, when yeast cells were transformed with the yeast genome library, about 11 transformants grew on the sucrose medium, indicating that invertase is secreted with the aid of the introduced translational fusion partners.

TABLE 1

| DNA introduced into Y2805 ΔgallΔinv2 (host cells) | Number of transformants | |
|---|---|---|
| | UD minimal medium (glucose) | YPSGA (sucrose) |
| — | 0 | 0 |
| pYHTS vectors | ~1 × 10⁴ | 0 |
| pYHTS + genomic library (*S. cerevisiae*) | ~1 × 10⁴ | 10 |
| pYHTS + genomic library (*H. polymorpha*) | ~1 × 10⁴ | 1 |

EXAMPLE 6

Analysis of Translational Fusion Partners

Transformants grown on the sucrose medium were cultured in YPD medium (1% yeast extract, 2% peptone, 2% glucose) for 24 hrs. After the cultured cells were harvested, they were lysed to isolate the introduced plasmids. The isolated plasmids were re-transformed into *E. coli*. Plasmids were isolated again from the transformed *E. coli*, assessed for gene insertion by restriction mapping, and subjected to DNA sequencing analysis. As a result, the plasmids were found to contain four genes having different sequences, which served as translational fusion partners (Table 2: novel translational fusion partners inserted into plasmids isolated from transformants having grow in sucrose medium).

6-1. Translational Fusion Partner 1 (TFP1)

The present inventors found translational fusion partner 1 (TFP1) (SEQ ID NO. 2) to be capable of effectively secreting a fusion protein of IL-2 and invertase into the extracellular environment. The TFP1 gene was identical to a yeast *S. cerevisiae* gene Yar066w. The Yar066w gene is similar to the α-1,4-glucan-glucosidase (STA1) gene and encodes a protein containing a glycosyl-phosphatidylinositol (GPI) anchor. The Yar066w gene, which is of unknown function, has 70.3% and 72.7% sequence similarities to yeast *S. cerevisiae* genes of unknown function, Yol155c and Yil169c, respectively. In an amino acid sequence encoded by the Yar066w gene, the region fused to IL-2 consisted of 105 amino acid residues among the total number of 203 amino acid residues, and contained a secretory signal of 23 amino acid residues for protein secretion, an N-glycosylation site and a serine/alanine-rich sequence.

6-2. Translational Fusion Partner 2 (TFP2)

The present inventors found translational fusion partner 2 (TFP2) (SEQ ID NO. 4) to be capable of effectively secreting a fusion protein of IL-2 and invertase into the extracellular environment. The TFP2 gene was identical to a yeast *S. cerevisiae* gene Yar026c. The Ya026c gene is of unknown function. In an amino acid sequence encoded by the Yar026c gene, the region fused to IL-2 consisted of 117 amino acid residues among the total number of 169 amino acid residues, and contained a secretory signal of 19 amino acid residues for protein secretion and three N-glycosylation sites.

6-3. Translational Fusion Partner 3 (TFP3)

The present inventors found translational fusion partner 3 (TFP3) (SEQ ID NO. 6) to be capable of effectively secreting a fusion protein of IL-2 and invertase into the extracellular environment. The TFP3 gene was identical to a yeast *S. cerevisiae* gene Yjl158c (PIR4/CIS3). The Yjl158c gene encodes an O-mannosylated protein covalently linked to the cell wall. The Yjl158c gene is known as a multicopy suppressor for a mutant deficient in the Cik1 gene participating in cell division. In an amino acid sequence encoded by the Yjl158c gene, the region fused to IL-2 consisted of 104 amino acid residues among the total number of 227 amino acid residues, and contained a pre-secretory signal of 23 amino acid residues and a pro-secretory signal of 41 amino acid residues for protein secretion, a Kex2p cleavage site containing a sequence of Lys-Arg, and a PIR repeat sequence.

6-4. Translational Fusion Partner 4 (TFP4)

The present inventors found translational fusion partner 4 (TFP4) (SEQ ID NO. 8) to be capable of effectively secreting a fusion protein of IL-2 and invertase into the extracellular environment. The TFP4 gene is derived from *Hansenula polymorpha* and is of unknown function. The region fused to IL-2 consisted of 50 amino acid residues, which contained a protein secretory signal of 18 amino acid residues.

TABLE 2

| Plasmids | Translational fusion partners | Yeast genes | Number of fused amino acids (total amino acid number) | Characteristics |
|---|---|---|---|---|
| pYHTS-TFP1 | TFP1 | Yar066w | 105 (203) | PRE, N-gly, Ser-rich, GPI |
| pYHTS-TFP2 | TFP2 | Yar026c | 117 (169) | PRE, N-gly |
| pYHTS-TFP3 | TFP3 | Yjl158c | 104 (227) | PRE-PRO, O-gly, PIR |
| pYHTS-TFP4 | TFP4 | Unknown | 50 (unknown) | PRE |

EXAMPLE 7

Analysis of Fusion Proteins Secreted into Culture Medium

Figure 7:
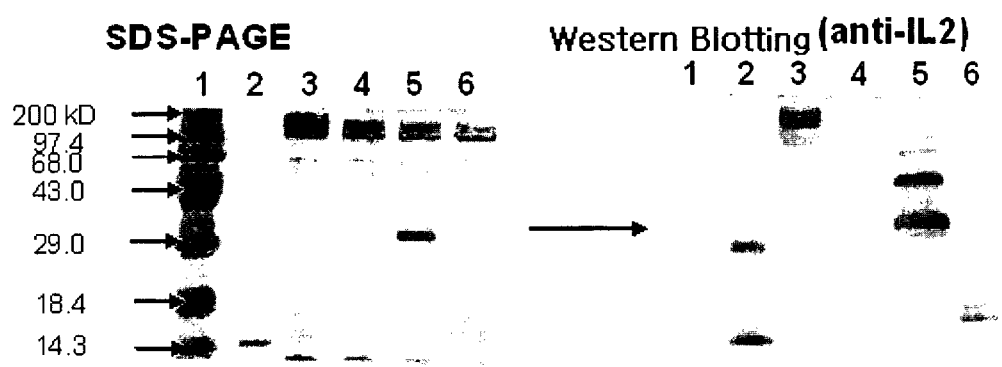
FIG. 7 shows the results of SDS-PAGE and Western blotting for culture supernatants of yeast cells containing any of four translational fusion partners (lane 1: size marker; lane 2: interleukin-2; lane 3: culture supernatant of yeast cells containing pYIL-TFP1; lane 4: culture supernatant of yeast cells containing pYIL-TFP2; lane 5: culture supernatant of yeast cells containing pYIL-TFP3; and lane 6: culture supernatant of yeast cells containing pYIL-TFP4)
Figure 8:
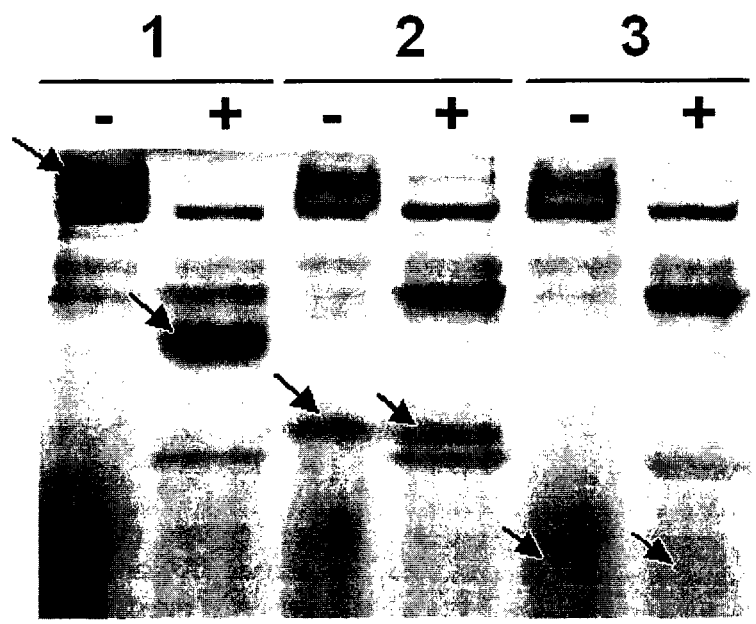
FIG. 8 shows the results of glycosylation analysis by Endo-H digestion, wherein samples are analyzed on SDS-PAGE (lane 1 (−): culture supernatant of yeast cells containing pYIL-TFP1, not treated with Endo-H; lane 1 (+) : culture supernatant of yeast cells containing pYIL-TFP1, treated with Endo-H; lane 2 (−): culture supernatant of yeast cells containing pYIL-TFP3, not treated with Endo-H; lane 2 (+): culture supernatant of yeast cells containing pYIL-TFP3, treated with Endo-H; lane 3 (−): culture supernatant of yeast cells containing pYIL-TFP4, not treated with Endo-H; and lane 3 (+) : culture supernatant of yeast cells containing pYIL-TFP4, treated with Endo-H)

To assess proteins secreted by yeast cells grown in a sucrose medium, yeast cells containing the four translational fusion partners described in Example 6 were cultured in YPDG medium (1% yeast extract, 2% peptone, 2% glucose, 0.3% galactose) for 40 hrs. After cells were removed, total proteins dissolved in the remaining culture supernatant were precipitated with acetone (final concentration: 40%) and analyzed by SDS-PAGE. However, each translational fusion partner did not appear as a single band because it had excessive glycosylation at a state of being fused to invertase. To solve this problem, invertase was removed from each vector (pYHTS-TFP1, 2, 3 and 4), and a translational termination codon was introduced into the IL-2 gene. In brief, to obtain a fragment including an IL-2 gene containing a GAL promoter, a TFP and a translational termination codon from each vector, PCR was carried out using a set of primers, JH132 (SacI-GAL-forward primer) (SEQ ID NO. 23) and JH137 (IL2-Term-reverse primer) (SEQ ID NO. 24). The amplified gene fragments were individually digested with SacI/SalI and inserted into a SacI/SalI-digested YEGα-HIR525 vector, thus generating pYIL-TFP1, 2, 3 and 4. The four IL-2 expression vectors were individually transformed into yeast cells. The resulting single colonies were cultured according to the same methods as described above, and the culture supernatants were analyzed by SDS-PAGE (FIG. 7). As shown in FIG. 7, strong protein bands having different sizes were found in the culture supernatants of yeast cells containing the IL-2 expression vectors except for pYIL-TFP2. These bands were confirmed by Western blotting using an anti-IL-2 antibody (FIG. 7), thus indicating that each secretion-inducing fusion protein is present at a state of being fused to IL-2. However, the size of the fusion proteins on SDS-PAGE was different from that predicted from the molecular weights of each translational fusion partner and the IL-2 gene. This difference was considered to be due to glycosylation of the fusion protein. Thus, each fusion protein was digested with Endo-H and analyzed by SDS-PAGE (FIG. 8). On an amino acid sequence, TFP1 was found to have one consensus N-glycosylation sequence (amino acid residues 28-30), and TFP3 contained a consensus O-glycosylation sequence. TFP4 was found to have no glcosylation sequence. As predicted, in the case of the protein expressed by the pYIL-TFP1, a great decrease was found in molecular weight after Endo-H digestion, indicating that the protein expressed by the pYIL-TFP1 is N-glycosylated. In contrast, there was no change in molecular weight of the protein expressed by the pYIL-TFP3 upon Endo-H digestion because the protein is O-glycosylated. Also, there was no change in molecular weight of the protein expressed by the pYIL-TFP4.

EXAMPLE 8

Production of Authentic Proteins by Kex2p Cleavage in Cells

In order to produce the TFP-IL-2 fusion proteins, which were expressed by the vectors used in Example 7 and secreted into the medium, in the authentic form identical to native human IL-2, a cleavage site (Leu-Asp-Lys-Arg) recognized by Kex2p protease, which yeast cells themselves produce, was inserted between a TFP and IL-2 so as to automatically remove the TFP from cells. To introduce a Kex2p cleavage site into the pYIL-TFP1, PCR was carried out using the pYIL-TFP1 as a template with each of two sets of primers, JH132 (SEQ ID NO. 23) and HY22 (TFP1-LDKR-reverse primer) (SEQ ID NO. 25), and HY23 (TFP1-LDKR-forward primer) (SEQ ID NO. 26) and JH137 (SEQ ID NO. 24). A secondary PCR was carried out using as templates the amplified products, a fragment containing a. GAL promoter and TFP1 and another fragment containing the IL-2 gene, which were electrophoresed and recovered from a gel, with a set of primers, JH132 (SEQ ID NO. 23) and JH137 (SEQ ID NO. 24). The secondarily amplified GAL promoter-TFP1-IL2 fragment was digested with SacI/SalI and inserted into a SacI/SalI-digested YEGα-HIR525 vector, thus generating pYIL-KRTFP1. Also, to introduce a Kex2p cleavage site into the pYIL-TFP2, according to the same method as described above, PCR was carried out using the pYIL-TFP2 as a template with two sets of primers, JH132 (SEQ ID NO. 23) and HY20 (TFP2-LDKR-reverse primer) (SEQ ID NO. 27), and HY21 (TFP2-LDKR-forward primer) (SEQ ID NO. 28) and JH137 (SEQ ID NO. 24). A secondary PCR was carried out using two amplified gene fragments as templates with a set of primers, JH132 (SEQ ID NO. 23) and JH137 (SEQ ID NO. 24). The secondarily amplified fragment was digested with SacI/SalI and inserted into a SacI/SalI-digested YEGα-HIR525 vector, thus generating pYIL-KRTFP2. Further, to introduce a Kex2p cleavage site into the pYIL-TFP3, according to the same method as described above, PCR was carried out using the pYIL-TFP3 as a template with two sets of primers, JH132 (SEQ ID NO. 23) and HY17 (TFP3-LDKR-reverse primer) (SEQ ID NO. 38), and HY18 (TFP3-LDKR-Forward primer) (SEQ ID NO. 39) and JH137 (SEQ ID NO. 24). A secondary PCR was carried out using two amplified gene fragments as templates with a set of primers, JH132 (SEQ ID NO. 23) and JH137 (SEQ ID NO. 24). The secondarily amplified fragment was digested with SacI/SalI and inserted into a SacI/SalI-digested YEGα-HIR525 vector, thus generating pYIL-KRTFP3. Yet further, to introduce a Kex2p cleavage site into the pYIL-TFP4, according to the same method as described above, PCR was carried out using the pYIL-TFP4 as a template with two sets of primers, JH132 (SEQ ID NO. 23) and HY24 (TFP4-LDKR-reverse primer) (SEQ ID NO. 29), and HY25 (TFP4-LDKR-forward primer) (SEQ ID NO. 30) and JH137 (SEQ ID NO. 24). A secondary PCR was carried out using two amplified gene fragments as templates with a set of primers, JH132 (SEQ ID NO. 23) and JH137 (SEQ ID NO. 24). The secondarily amplified fragment was digested with SacI/SalI and inserted into a SacI/SalI-digested YEGα-HIR525 vector, thus generating pYIL-KRTFP4.

Figure 9:
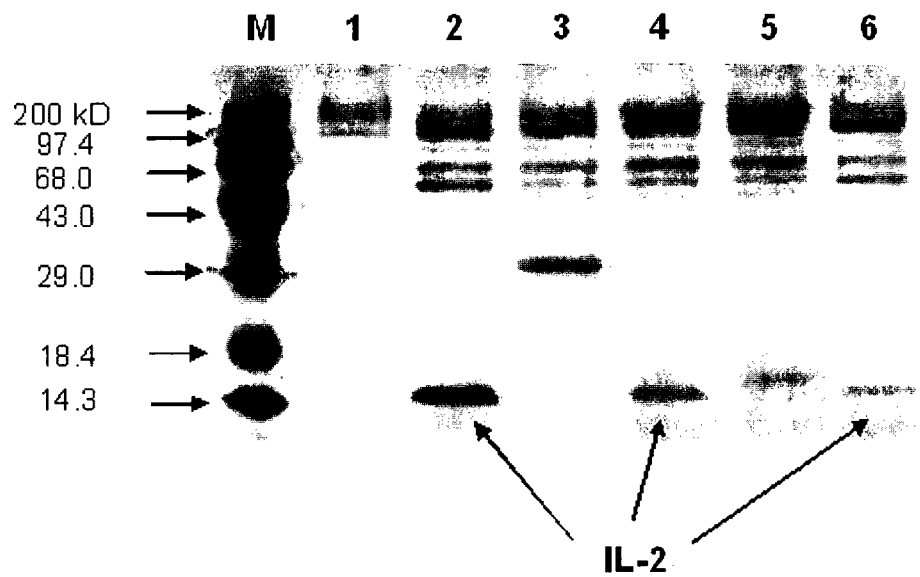
FIG. 9 shows the results of SDS-PAGE of culture supernatants of yeast cells according to the presence or absence of a Kex2p possessing site (lane M: size marker, lane 1: culture supernant of yeast cells containing pYIL-TFP1; lane 2: culture supernant of yeast cells containing pYIL-KRTFP1; lane 3: culture supernant of yeast cells containing pYIL-TFP3; lane 4: culture supernant of yeast cells containing pYIL-KRTFP3; lane 5: culture supernant of yeast cells containing pYIL-TFP4; and lane 6: culture supernant of yeast cells containing pYIL-KRTFP4)

Among the four vectors, pYIL-KRTFP1, pYIL-KRTFP3 and pYIL-KRTFP4 were individually introduced into a yeast 2805Δgal1Δinv2 strain. Single colonies were picked and cultured in YPDG medium (1% yeast extract, 2% peptone, 2% glucose, 0.3% galactose) for 40 hrs. After cells were removed, the remaining culture supernatants were subjected to SDS-PAGE. As shown in FIG. 9, secreted proteins were found to have the same size as native human IL-2. Among the three TFPs inducing the secretory production of human IL-2, TFP1 was found to be most effective in the secretory production of authentic IL-2.

The pYIL-KRTFP1, pYIL-KRTFP2, pYIL-KRTFP3 and pYIL-KRTFP4 vectors were deposited at an international depository authority, KCTC (Korean Collection for Type Cultures; 52, Oun-dong, Yusong-ku, Taejon, Korea) on Nov.

11, 2003, and assigned accession numbers KCTC 10544BP, 10545BP, 10546BP and 10546BP, respectively.

EXAMPLE 9

Analysis of Characteristics of the Translational Fusion Partner 1 (TFP1)

Figure 10:
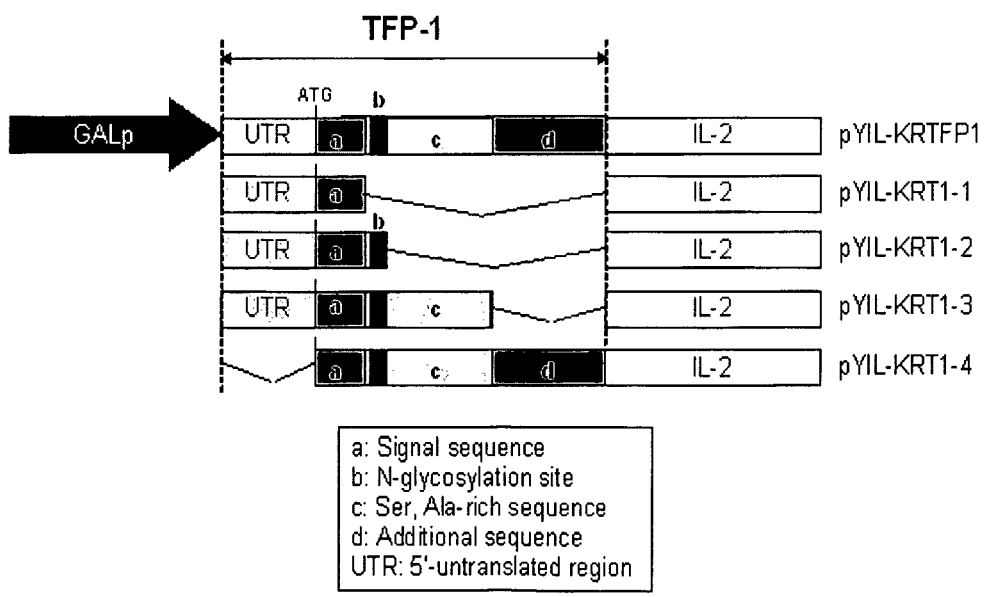
FIG. 10 is a schematic presentation of plasmids from which the TFP1 gene has been partially deleted for the analysis of characteristics of TFP1.

The TFP1, identified as a translational fusion partner most effectively inducing the secretory production of IL-2, was assessed to determine whether any of specific sequences present on the TFP1 sequence, a secretory signal (a), an N-glycosylation site (b), a serine/alanine-rich sequence (c), an additional sequence (d) and a 5'-UTR (5'-untranslated region) (e), directly affects the secretion of the non-producible protein IL-2. To do this, as shown in FIG. 10, deletion mutants of the TFP1 gene, in which each specific sequence was deleted, were prepared. First, to remove the additional sequence (d) having no unique property from the TFP1 sequence, PCR was carried out using the pYIL-KRTFP1 as a template with a set of primers, JH143 (XbaI-TFP1-d-reverse primer) (SEQ ID NO. 31) and JH132 (SEQ ID NO. 23). The amplified DNA fragment contained the TFP1-1, which was deleted in the GAL promoter and the (d) sequence of the TFP1 sequence. To remove the additional sequence (d) and the serine/alanine-rich sequence (c) from the TFP1 sequence, PCR was carried out using the pYIL-KRTFP1 as a template with a set of primers, JH142 (XbaI-TFP1-c-reverse primer) (SEQ ID NO. 32) and JH132 (SEQ ID NO. 23). The amplified fragment contained the TFP1-2, which was deleted in the GAL promoter, the (c) sequence and the (d) sequence. Also, to remove the (d) sequence, the (c) sequence and the N-glycosylation site (b) from the TFP1 sequence, PCR was carried out using the pYIL-KRTFP1 as a template with a set of primers, JH141 (XbaI-TFP1-b-reverse primer) (SEQ ID NO. 33) and JH132 (SEQ ID NO. 23). The amplified fragment contained the TFP1-3, which was deleted in the GAL promoter and the sequences (c), (d) and (b). To introduce a Kex2p cleavage site into the IL-2 gene, PCR was carried out using the pYIL-KRTFP1 as a template with a set of primers, JH140 (SpeI-XbaI-LDKR-forward primer) (SEQ ID NO. 34) and JH137 (SEQ ID NO. 24). The amplified IL-2 fragment was purified, digested with SpeI and SalI, and, along with each of the three obtained fragments (TFP1-1, 2 and 3) digested with SacI and XbaI, inserted into a YEGα-HIR525 vector predigested with SacI and SalI, thus generating, as shown in FIG. 10, pYIL-KRT1-1, pYIL-KRT1-2 and pYIL-KRT1-3, respectively. To remove the 5'-UTR of the TFP1, PCR was carried out using the pYIL-KRTFP1 as a template with a set of primers, HY38 (TFP1-UTR-forward primer) (SEQ ID NO. 35) and JH137 (SEQ ID NO. 24). The amplified gene was purified, digested with BamHI/SalI, and ligated along with a SacI/BamHI-digested GAL10 promoter into a SacI/SalI-digested YEGα-HIR525 vector, thus generating pYIL-KRT1-4 (FIG. 10).

Figure 11:
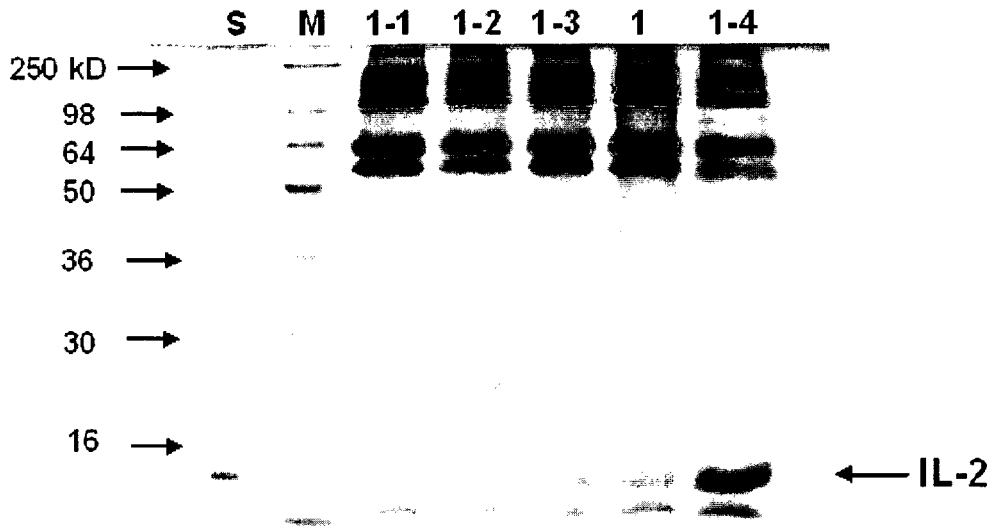
FIG. 11 shows the results of SDS-PAGE for analyzing the ability of TFP1-derived translational fusion partners (TFP-1, 2, 3 and 4) to secrete interleukin-2 (lane M: size marker; lane S: interleukin-2; lane 1-1: culture supernatant of yeast cells containing pYIL-KRT1-l(also, referred to as pYIL-KRTFP1-1); lane 1-2: culture supernatant of yeast cells containing pYIL-KRT1-2(also, referred to as pYIL-KRTFP1-2); lane 1-3: culture supernatant of yeast cells containing pYIL-KRT1-3(also, referred to as pYIL-KRTFP1-3); lane 1: culture supernatant of yeast cells containing pYIL-KRTFP1; and lane 1-4: culture supernatant of yeast cells containing pYIL-KRT1-4(also, referred to as pYIL-KRTFP1-4))

The four plasmids, pYIL-KRT1-1, pYIL-KRT1-2, pYIL-KRT1-3 and pYIL-KRT1-4, were transformed into yeast cells. Single colonies were cultured, and culture supernatants were subjected to SDS-PAGE. As shown in FIG. 11, an IL-2 band was found only in a culture supernatant of cells transformed with the pYIL-KRT1-3 containing all of the secretory sequence, the N-glycosylation site and the serine/alanine-rich sequence. The IL-2 band was not observed in culture supernatants of cells transformed with the pYIL-KRT1-2 deleted for the serine/alanine-rich sequence and cells transformed with the pYIL-KRT1-1 deleted in both the serine/alanine-rich sequence and the N-glycosylation site. These results indicate that three characteristic sequences (the secretory sequence, the N-glycosylation site and the serine/alanine-rich sequence) present in the TFPL are required for effectively inducing IL-2 secretion. Also, when the TFP1 was deleted in its 5'-UTR, protein expression levels increased more than about three times.

The pYIL-KRT1-3 and pYIL-KRT1-4 vectors were deposited at an international depository authority, KCTC (Korean Collection for Type Cultures; 52, Oun-dong, Yusong-ku, Taejon, Korea) on Nov. 11, 2003, and assigned accession numbers KCTC 10548BP and 10549BP, respectively.

EXAMPLE 10

Fermentation Production of Human IL-2 using the Translational Fusion Partner TFP1-4

Figure 12:
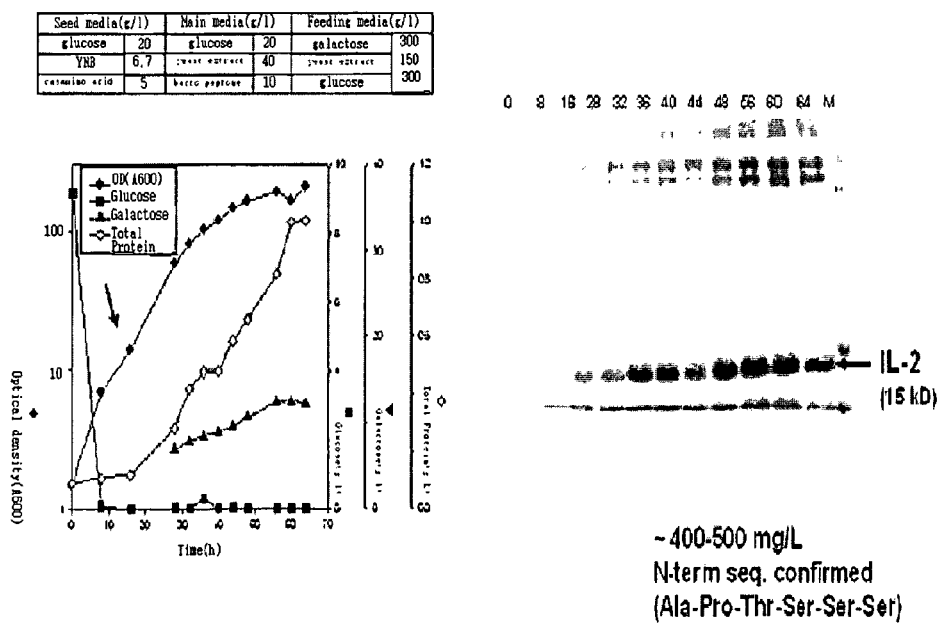
FIG. 12 shows a profile for fed-batch fermentation of a recombinant yeast strain containing pYIL-KRT1-4 and the results of SDS-PAGE for analyzing proteins secreted into the medium according to fermentation time.

A recombinant yeast strain transformed with the pYIL-KRT1-4 vector was cultured in a 5-L jar fermentor by fed-batch culture to be evaluated for its ability to induce the secretory production of IL-2. A seed culture to be inoculated in the fermentor was cultured in a flask using a seed culture medium (6.7% yeast nitrogen base without amino acids, 0.5% casamino acids and 2% glucose). When the culture using a fermentation culture medium (4% yeast extract, 1% peptone, 2% glucose) as an initial fermentation medium reached an OD600 of about 15, a fed-batch medium (15% yeast extract, 30% glucose, 30% galactose) was supplied with various amounts according to cell growth rates. After a culture period of about 64 hrs, the culture reached an OD600 of about 200. 5 µl of the medium was collected at the given time points and assessed for secreted proteins by SDS-PAGE (FIG. 12). Compared to a standard sample, about 500 mg/L of IL-2 was found to be secreted into the medium. The IL-2 produced as a secretory product in the yeast fermentation was found to have an amino-terminal sequence of Ala-Pro-Thr-Ser-Ser-Ser through amino-terminal sequence analysis, indicating that it is identical to the native IL-2 secreted in the human body.

EXAMPLE 11

Comparison of the Translational Fusion Partners TFP1 to 4 for their Capacity to Secrete Human G-CSF In order to determine whether the four translational fusion partners (TFP1, 2, 3 and 4) obtained using the non-producible protein human IL-2 are effective in the secretion of other non-producible human proteins, each of the four TFPs was fused to a non-producible protein, human G-CSF, expressed in yeast cells and assessed for its secretion. The human G-CSF gene was obtained as follows. PCR was carried out using a human cDNA library with a set of primers, JH144 (GCSF-forward primer) (SEQ ID NO. 36) and JH145 (GCSF-reverse primer) (SEQ ID NO. 37). The amplified gene was digested with XbaI/SalI and inserted into the XbaI/SalI sites of each of pYIL-KRTFP1, 2, 3 and 4, thus generating pYGCSF-TFP1, 2, 3 and 4.

Figure 13:
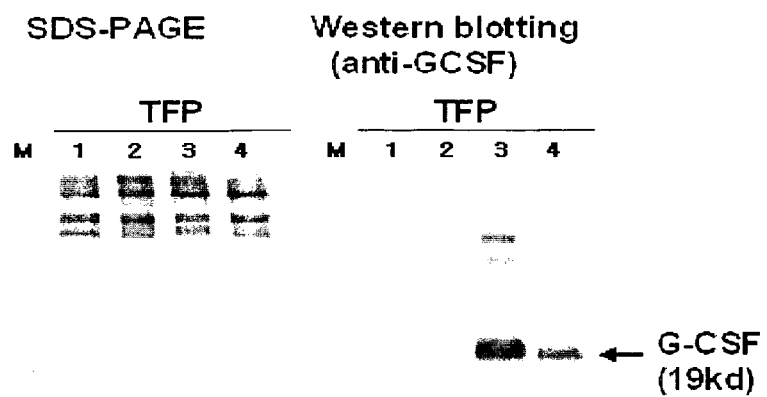
FIG. 13 shows the results of SDS-PAGE and Western blotting, displaying that translational fusion partners TFP1, 2, 3 and 4 induce the secretion of a non-producible protein human G-CSF (lane M: size marker; lane 1: culture supernatant of yeast cells containing pYGCSF-KRTFP1; lane 2: culture supernatant of yeast cells containing pYGCSF-KRTFP2; lane 3: culture supernatant of yeast cells containing pYGCSF-KRTFP3; and lane 4: culture supernatant of yeast cells containing pYGCSF-KRTFP4)

To express human G-CSF in yeast cells, the PYGCSF-TFP1, 2, 3, and 4 vectors were transformed into yeast cells. Single colonies were isolated and cultured, the culture supernatants were subjected to SDS-PAGE and Western blotting using an anti-G-CSF antibody. The results are given in FIG. 13. G-CSF was produced as a secretory product by each of the TFPs, and TFP1 and TFP3 were found to effectively induce the secretory production of G-CSF. In particular, Western blotting with an anti-G-CSF antibody (Chemicon, USA)

demonstrated that TPF3 is most effective in the secretory production of G-CSF. Thus, because each of the four TFPs was demonstrated to exert maximal secretion efficiency according to the type of protein, the four TFPs of the present invention were considered to be very useful as translational fusion partners capable of secreting various non-producible proteins other than IL-2 and G-CSF.

EXAMPLE 12

Fermentation Production of Human G-CSF using the Translational Fusion Partner TFP3

Figure 14:
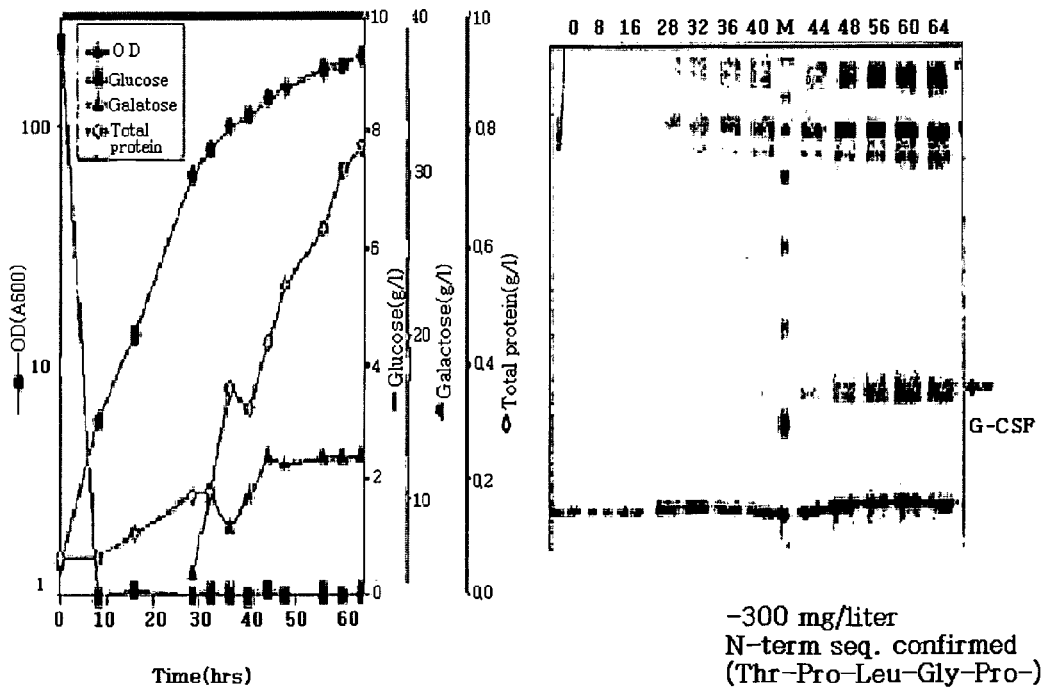
FIG. 14 shows a profile for fed-batch fermentation of a recombinant yeast strain containing pYGCSF-TFP3 and the results of SDS-PAGE for analyzing proteins secreted into the medium according to fermentation time.

A recombinant yeast strain transformed with the pYGCSF-TFP3 vector prepared in Example 11 was cultured in a 5-L jar fermentor by fed-batch culture to be evaluated for its ability to induce the secretory production of human G-CSF. A seed culture to be inoculated in the fermentor was cultured in a flask using a seed culture medium (6.7% yeast nitrogen base without amino acids, 0.5% casamino acids and 2% glucose). When the culture using a fermentation culture medium (4% yeast extract, 1% peptone, 2% glucose) as an initial fermentation medium reached an OD600 of about 15, a fed-batch medium (15% yeast extract, 30% glucose, 30% galactose) was supplied in various amounts according to cell growth rates. After a culture period of about 64 hrs, the culture reached an OD600 of about 200. 5 μl of the medium was collected at the given time points and assessed for secreted proteins by SDS-PAGE (FIG. 14). Compared to a standard sample, about 300 mg/L of human G-CSF was found to be secreted into the medium. The human G-CSF produced as a secretory product in the yeast fermentation was found to have an amino-terminal sequence of Thr-Pro-Leu-Gly-Pro through amino-terminal sequence analysis, indicating that it is identical to the native G-CSF secreted in the human body.

EXAMPLE 13

Figure 15:
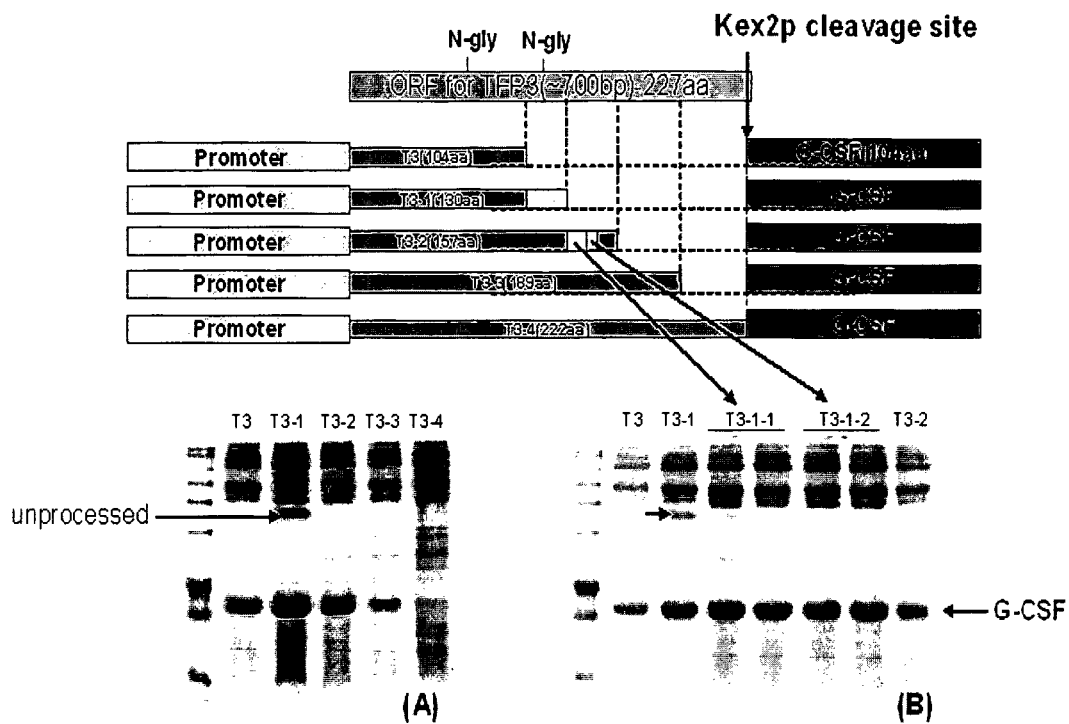
FIG. 15 shows the isolation of the full-length gene of which a translational fusion partner TFP3 is a part and the enhanced secretion of G-CSF through the modification of a fusion site between the isolated gene and the G-CSF gene ((A) lane T3: culture supernatant of yeast cells containing pYGCSF-KRTFP3, lane T3-1: culture supernatant of yeast cells containing pYGCSF-KRTFP3-1, lane T3-2: culture supernatant of yeast cells containing pYGCSF-KRTFP3-2, lane T3-3: culture supernatant of yeast cells containing pYGCSF-KRTFP3-3, and lane T3-4: culture supernatant of yeast cells containing pYGCSF-KRTFP3-4; and (B) lane T3: culture supernatant of yeast cells containing pYGCSF-KRTFP3, lane T3-1: culture supernatant of yeast cells containing pYGCSF-KRTFP3-1, lane T3-1-1: culture supernatant of yeast cells containing PYGCSF-KRTFP3-1-1, lane T3-1-2: culture supernatant of yeast cells containing pYGCSF-KRTFP3-1-2, and lane T3-2: culture supernatant of yeast cells containing pYGCSF-KRTFP3-2)

Analysis of Secretion Efficiency of Derivatives of the Translational Fusion Partner TPF3 for Human G-CSF Since TFP3 was found to be most effective for the optimal secretion of G-CSF in Example 11, the whole TFP3-derived gene, Yjl158c(CIS3), was obtained from the yeast Saccharomyces cerevisiae genome by PCR. As shown in FIG. 15, six TFP3 derivatives having different length, TFP3-1, 2, 3 and 4, TFP3-1-1 (SEQ ID NO. 40) and TFP3-1-2 (SEQ ID NO. 42), were prepared. The primarily obtained TFP3 consisted of 104 amino acids among a total of 227 amino acids of Yjl158c (CIS3). Products having gradually increased length, TFP3-1 (130 amino acids), TFP3-2 (157 amino acids), TFP3-3 (189 amino acids) and TFP3-4 (222 amino acids), were prepared. The TFP3 derivatives were individually linked to the G-CSF gene, and a Kex2p cleavage site was inserted into the fusion site. As shown in the A panel of FIG. 15, the TFP3-1, which additionally contained 26 amino acids compared to TFP3, increased the secretion of G-CSF about three fold because it contained an N-glycosyation site compared to TFP3. In contrast, when the length of TFP3 increased further, the secretion rates of G-CSF did not change, or a decrease in the secretion rates of G-CSF was found in the case of TFP3-3 and TFP3-4.

In addition, as shown in the A panel of FIG. 15, the unprocessed form of a TFP3-1-GCSF fusion protein, which was not completely cleaved by Kex2p, was secreted into the medium in a manner increasing with increasing expression and secretion efficiency. This was considered because sugar moieties added to a plurality of O-glycosylation sites present in the fusion site of the two genes interrupted the approach of Kex2p for cleavage of the fusion site. In this regard, TFP3-1-1 (134 amino acids), having an addition of 4 amino acids compared to TFP3, and TFP3-1-2 (143 amino acids), having an addition of 13 amino acids compared to TFP3, were prepared and assessed for their capacity to secrete G-CSF and the decrease in expression as a fusion form. As shown in the B panel of FIG. 15, fusion forms of TFP3-1-1 and TFP3-1-2 with G-CSF greatly decreased with no decrease in secretion of G-CSF. These results indicate that secretion rates of a target protein can be more enhanced by the elaborate manipulation of a fusion site between the target protein and each of the obtained TFPs.

Two G-CSF expression vectors, pYGT3-1-1-GCSF and pYGT3-1-2-GCSF containing the translational fusion partners TFP3-1-1 and TFP3-1-2, respectively, were deposited at an international depository authority, KCTC (Korean Collection for Type Cultures; 52, Oun-dong, Yusong-ku, Taejon, Korea) on Dec. 21, 2004, and assigned accession numbers KCTC 10753BP and KCTC 10754BP, respectively.

EXAMPLE 14

Secretory Production of an Industrial Enzyme Lipase using the Translational Fusion Partner TFP3

A CalB gene obtained by XbaI/SalI digestion of pYGA-CalB14 (E S Choi, Korea Research Institute of Bioscience and Biotechnology) was inserted into the XbaI/SalI sites of the G-CSF expression vector, pYGCSF-KRTFP3, thus generating pYGT3-CalB14. The pYGT3-CalB14 vector was compared with the pYGA-CalB14 vector for secretion rates of CalB14 according to culture temperature. When CalB14 was produced as a secretory product using TFP3, it was secreted a rate of more than two times higher than the conventional expression system at an optimal culture temperature of 30° C. (Table 3: CalB activity according to culture temperature of yeast cells containing each expression vector)

TABLE 3

|  | Lipase activity | |
| --- | --- | --- |
|  | 30° C. | 22° C. |
| pYGA-CalB14 (AMY) | 295 | 885 |
| pYGT3-CalB14 (TFP3) | 1922 | 874 |

Figure 16:
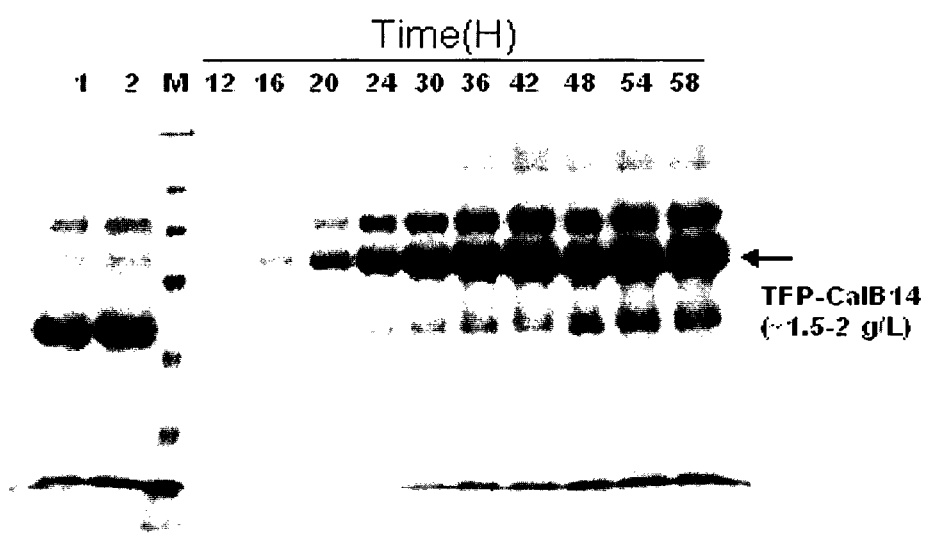
FIG. 16 shows the results of SDS-PAGE of fermentation media for the secretory production of an industrial enzyme CalB14 by a translational fusion partner TFP3 (lane M: size marker; lanes 1 and 2: culture supernatant of yeast cells containing pYGA-CalB14 at a low temperature of 20° C.; and lanes 12-58: culture supernatant of yeast cells containing pYGT3-CalB14)

A recombinant yeast strain containing the pYGT3-CalB14 vector was cultured in a 5-L jar fermentor at an optimal temperature of 30° C. by fed-batch culture to be evaluated for its ability to induce the secretory production of CalB14. When the culture using a fermentation culture medium (4% yeast extract, 1% peptone, 2% glucose) reached an OD600 of about 15, a fed-batch medium (15% yeast extract, 30% glucose, 30% galactose) was supplied with various amounts according to cell growth rates. The recombinant yeast strain very rapidly grew and secreted CalB14 into the medium with high efficiency without a change in culture temperature. Analysis of protein activity and concentration revealed that about 1.5-2.0 g/L of CalB14 is secreted into the medium, thereby making the cost-effective large-scale production of CalB14 possible (FIG. 16).

EXAMPLE 15

Evaluation of the Activity of the Translational Fusion Partner TFP1 in *Pichia pastoris*

In order to determine whether the TFPs developed in the present invention are functional in another yeast, *P. pastoris*, another yeast *P. pastoris* vector, pPIC9 (Invitrogen, USA), was digested with BglII/EcoRI to eliminate the AOX promoter, where a GAP (glyceraldehyde 3-phosphate dehydrogenase) promoter, obtained using a BglII-GAP-forward primer (SEQ ID NO. 44) and a GAP-EcoRI-reverse primer (SEQ ID NO. 45), was inserted, thus generating pPIC9-GAP. This vector was digested with EcoRI-NotI and ligated with each of EcoRI-NotI-digested Mfalpha (mating factor alpha)-GCSF and TFP1-GCSF genes, thus yielding PGAP-MF-GCSF and pGAP-TFP1-GCSF. These vectors were individually digested with SalI and transformed into *P. pastoris* GS115 (Invitrogen, USA). The transformed cells were cultured in flasks, and culture supernatants were analyzed by SDS-PAGE for G-CSF secretion to select final transformants.

Figure 17:
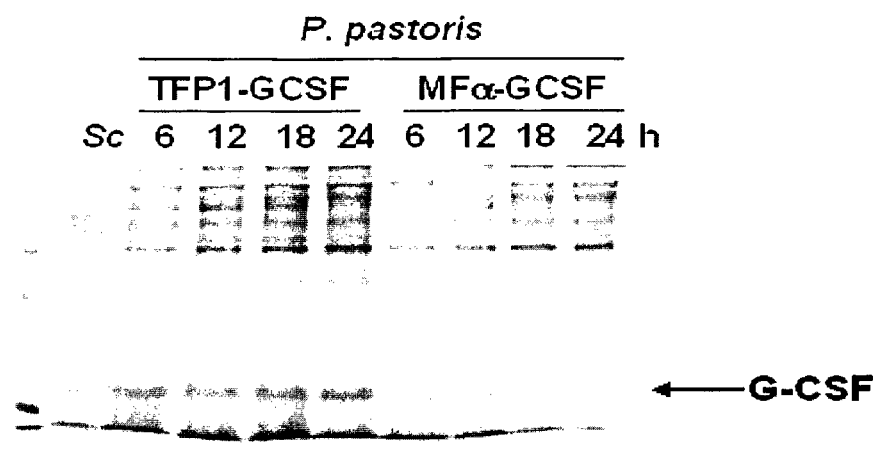
FIG. 17 shows the results of SDS-PAGE of samples collected at given time points upon fetch culture of *Pichia pastoris* containing a G-CSF expression vector containing a translational fusion partner TFP1, pGAP-TFP1-GCSF, or a conventional G-CSF expression vector pGAP-MFalpha-GCSF (lane Sc: 10 μl of a culture supernatant of yeast *S. cerevisiae* containing pYGCSF-KRTFP1; and lanes 6-24: concentrates of 200 μl of culture supernatants of *P. pastoris* containing pGAP-TFP1-GCSF or pGAP-MFalpha-GCSF)
Figure 18:
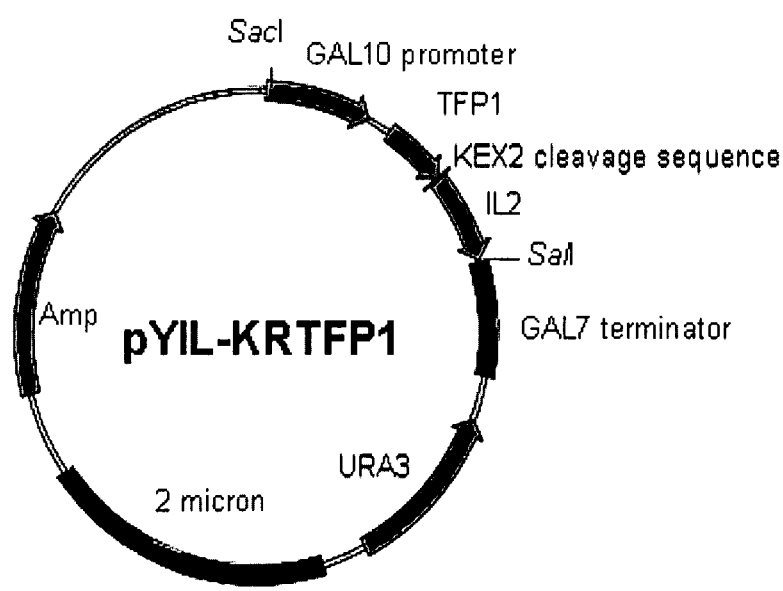
FIG. 18 is a schematic map of pYIL-KRTFP1.
Figure 19:
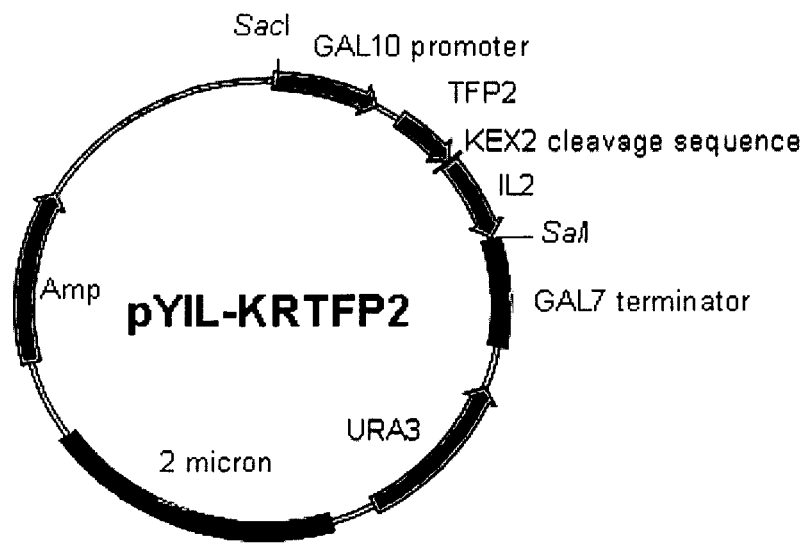
FIG. 19 is a schematic map of pYIL-KRTFP2.
Figure 20:
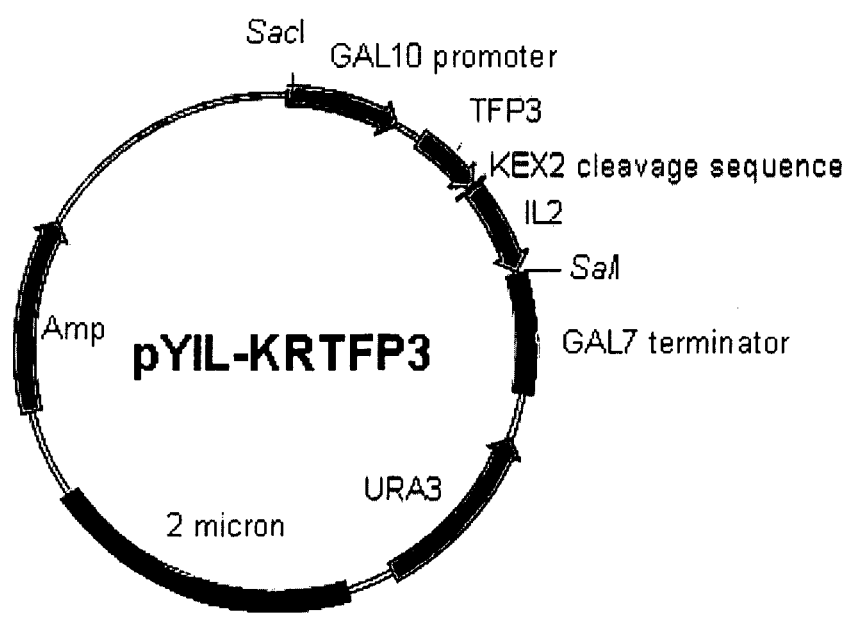
FIG. 20 is a schematic map of pYIL-KRTFP3.
Figure 21:
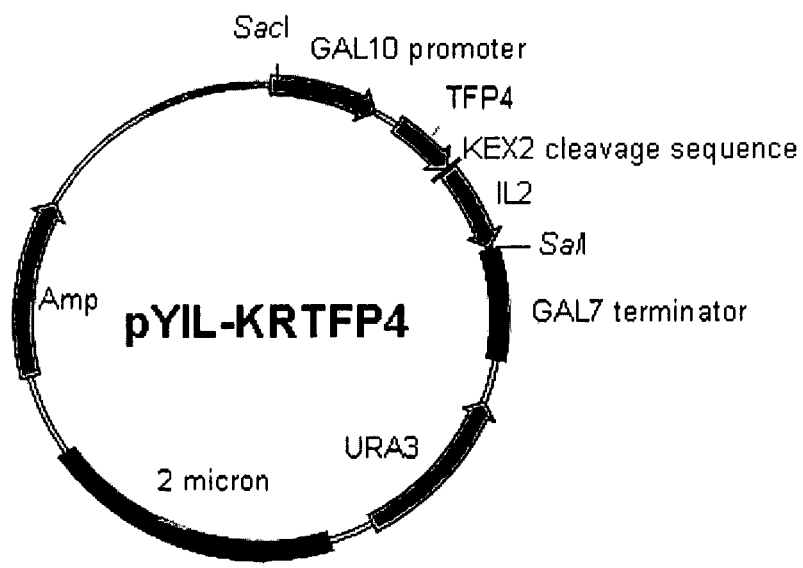
FIG. 21 is a schematic map of pYIL-KRTFP4.
Figure 22:
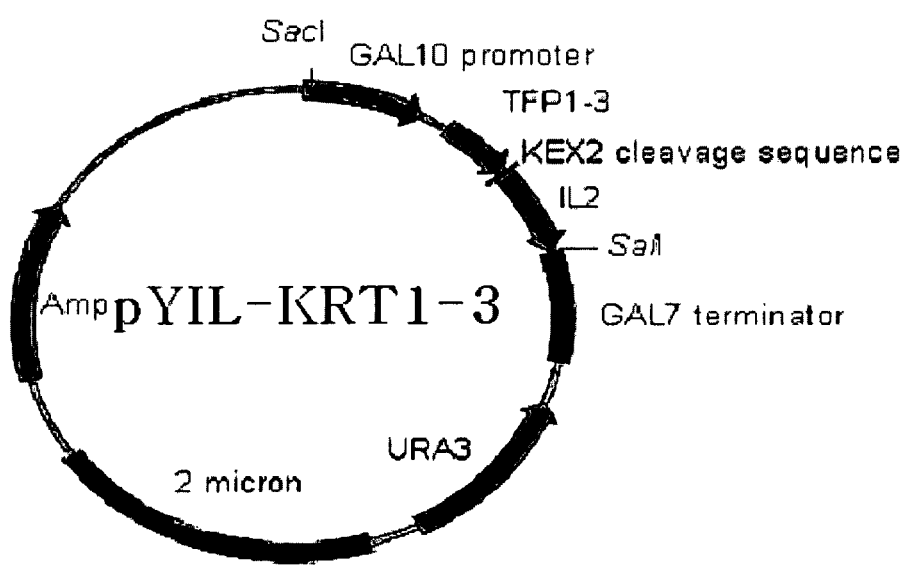
FIG. 22 is a schematic map of pYIL-KRT1-3(also, referred to as pYIL-KRTFP1-3)
Figure 23:
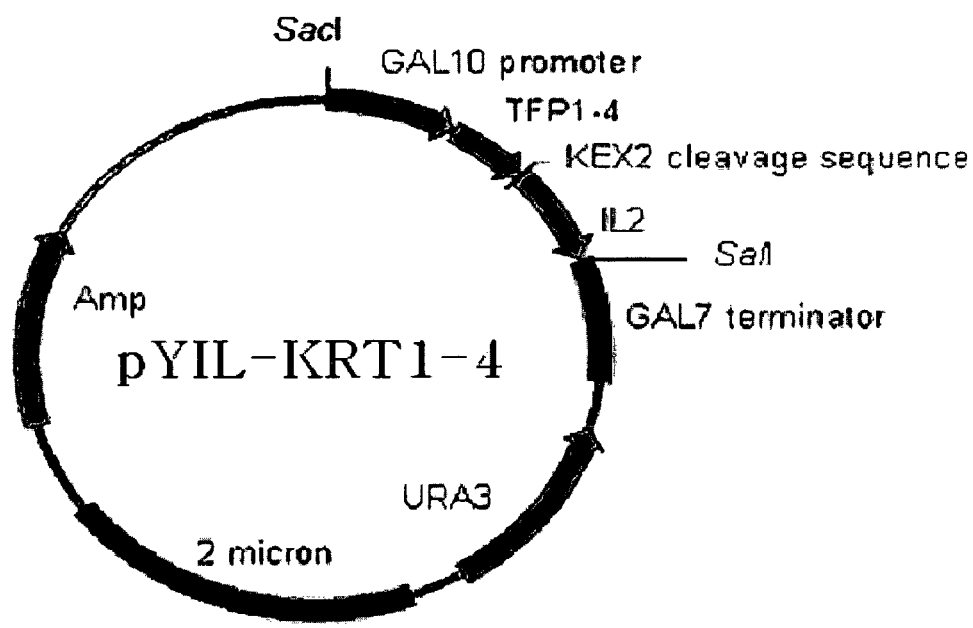
FIG. 23 is a schematic map of pYIL-KRT1-4(also, referred to as pYIL-KRTFP1-4)
Figure 24:
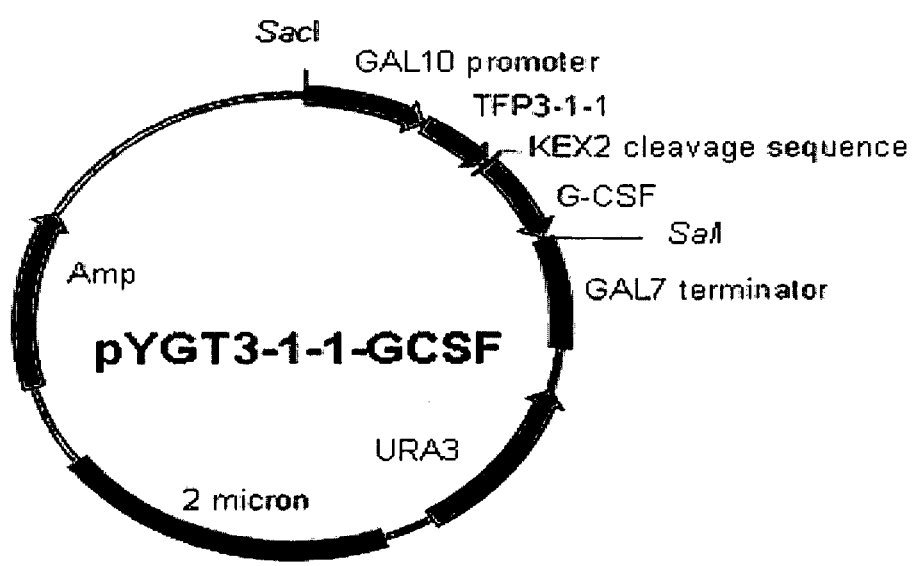
FIG. 24 is a schematic map of pYGT3-1-1-GCSF.
Figure 25:
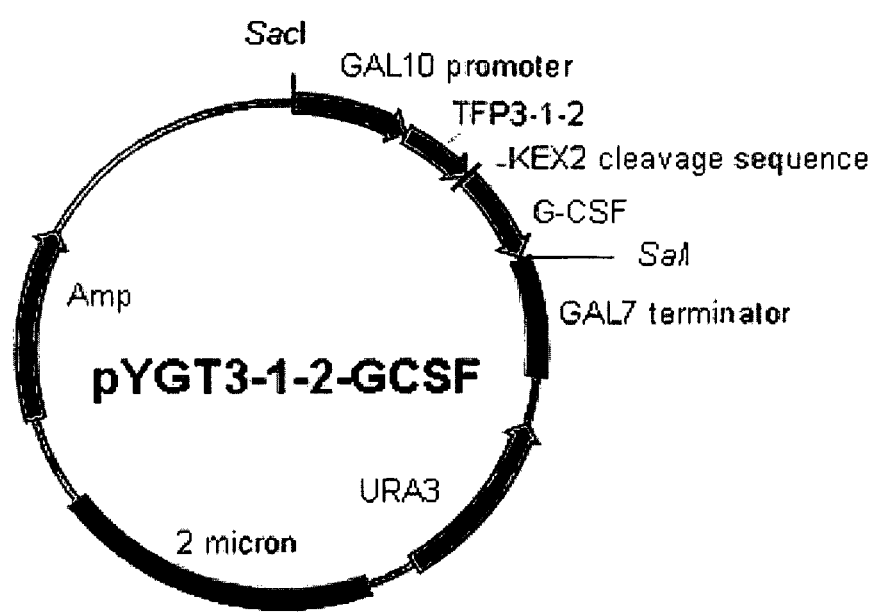
FIG. 25 is a schematic map of pYGT3-1-2-GCSF.

The selected transformants transformed with each of the vectors were batch-cultured in a fermentor using a fermentation medium (4% yeast extract, 1% bactopeptone, 4% glycerol). Samples were collected at given time points, and secretion of G-CSF was analyzed by SDS-PAGE (FIG. 17). As shown in FIG. 17, TFP1 had higher secretion efficiency than Mfalpha. These results indicate that yeast *S. cerevisiae*-derived TFPs are also very useful in *P. pastoris*.

Industrial Applicability

The present invention allows the cost-effective large-scale production of various proteins that are not able to recombinantly produce or are expressed in low levels through the rapid screening and use of suitable TFPs.

The invention claimed is:

1. A method for identifying a translational fusion partner (TFP) capable of stimulating secretion of a non-producible target protein, the method comprising:
    a) preparing an automatic screening vector comprising a polynucleotide encoding a fusion polypeptide that comprises said non-producible target protein linked to a reporter protein;
    b) linking a polynucleotide fragment to said automatic screening vector to create a library;
    c) transforming said library into host cells having no activity of said reporter protein prior to transformation;
    d) culturing said host cells; and
    e) identifying whether the polynucleotide fragment linked to said automatic screening vector comprises said TFP by detecting activity of said reporter protein which is secreted from one or more of said host cells.

2. The method of claim 1, further comprising a step of isolating the identified TFP.

3. The method of claim 1, wherein said target protein is selected from the group consisting of cytokines, serum proteins, immunoglobulins, cytokine receptors, lactoferrin, interferons, colony stimulating factors, stem cell factor, phospholipase activating protein, insulin, tumor necrosis factor, growth factors, hormones, enzymes, anticancer peptides, and antibiotic peptides.

4. The method of claim 1, wherein said target protein is human interleukin-2, human granulocyte colony stimulating factor, or CalB14.

5. The method of claim 1, wherein said plurality of polynucleotide fragments is from genomic DNA.

6. The method of claim 1, wherein said plurality of polynucleotide fragments is from cDNA.

7. The method of claim 1, wherein said plurality of polynucleotide fragments is from animal, plant, or microorganism DNA.

8. The method of claim 7, wherein said plurality of polynucleotide fragments is from yeast DNA.

9. The method of claim 7, wherein said plurality of polynucleotide fragments is from *Candida, Debaryomyces, Hansenula, Kluyveromyces, Pichia, Schizosaccharomyces, Yarrowia, Saccharomyces, Aspergillus, Penicillium, Rhizopus,* or *Trichoderma* DNA.

10. The method of claim 1, wherein said host cells are eucaryotic or bacterial cells.

11. The method of claim 10, wherein said host cells are *Escherichia, Pseudomonas, Bacillus, Streptomyces, Spodoptera frugiperda,* CHO, COS 1, COS 7, BSC 1, BSC 40, BMT 10, *Candida, Debaryomyces, Hansenula, Kluyveromyces, Pichia, Schizosaccharomyces, Yarrowia, Saccharomyces, Aspergillus, Penicillium, Rhizopus,* or *Trichoderma* cells.

12. The method of claim 1, wherein said reporter protein is an extracellularly secreted protein.

13. The method of claim 12, wherein said reporter protein is selected from the group consisting of invertase, sucrase, cellulase, xylanase, maltase, amylase, glucoamylase, and galactosidase.

14. The method of claim 13, wherein said reporter protein is invertase and said cell is cultured on medium containing only sucrose as a carbon source.

15. The method of claim 1, wherein said automatic screening vector further comprises a promoter.

16. The method of claim 15, wherein said promoter is from a gene selected from the group consisting of GAPDH, PGK, ADH, PHO5, GAL1, and GAL10.

17. The method of claim 1, wherein said automatic screening vector further comprises a cleavage recognition site.

18. The method of claim 17, wherein said cleavage recognition site is recognized by Kex2 p.

19. The method of claim 1, wherein said automatic screening vector comprises a promoter, a polynucleotide encoding a target protein, which is deleted for translation initiation and termination codons, and a polynucleotide encoding a reporter protein fused in frame to the polynucleotide encoding the target protein.

20. A method for identifying a translational fusion partner (TFP) capable of stimulating secretion of a non-producible target protein, the method comprising:
    a) preparing an automatic screening vector comprising a polynucleotide encoding a fusion polypeptide that comprises said non-producible target protein linked to invertase;
    b) linking a polynucleotide fragment to said automatic screening vector to create a library;
    c) transforming said library into a yeast mutant strain deleted for its endogenous invertase gene;
    d) culturing said yeast mutant strain on a medium containing only sucrose as a carbon source; and
    e) identifying said whether the polynucleotide fragment linked to said automatic screening vector comprises TFP by detecting activity of said invertase which is secreted from one or more of said yeast mutant strain.

* * * * *

SEQUENCE LISTING

```
<160> NUMBER OF SEQ ID NOS: 45

<210> SEQ ID NO 1
<211> LENGTH: 105
<212> TYPE: PRT
<213> ORGANISM: Saccharomyces cerevisiae
<220> FEATURE:
<221> NAME/KEY: PEPTIDE
<222> LOCATION: (1)..(105)
<223> OTHER INFORMATION: TFP1

<400> SEQUENCE: 1

Met Phe Asn Arg Phe Asn Lys Phe Gln Ala Ala Val Ala Leu Ala Leu
1               5                   10                  15

Leu Ser Arg Gly Ala Leu Gly Asp Ser Tyr Thr Asn Ser Thr Ser Ser
            20                  25                  30

Ala Asp Leu Ser Ser Ile Thr Ser Val Ser Ser Ala Ser Ala Ser Ala
        35                  40                  45

Thr Ala Ser Asp Ser Leu Ser Ser Ser Asp Gly Thr Val Tyr Leu Pro
    50                  55                  60

Ser Thr Thr Ile Ser Gly Asp Leu Thr Val Thr Gly Lys Val Ile Ala
65                  70                  75                  80

Thr Glu Ala Val Glu Val Ala Ala Gly Gly Lys Leu Thr Leu Leu Asp
                85                  90                  95

Gly Glu Lys Tyr Val Phe Ser Ser Asp
            100                 105

<210> SEQ ID NO 2
<211> LENGTH: 430
<212> TYPE: DNA
<213> ORGANISM: Saccharomyces cerevisiae
<220> FEATURE:
<221> NAME/KEY: gene
<222> LOCATION: (1)..(430)
<223> OTHER INFORMATION: TFP1

<400> SEQUENCE: 2
gatcgtcata ttcactcttg ttctcataat agcagtccaa gttttcatct ttgcaagctt      60
tactatttct ttcttttat tggtaaactc tcgcccatta caaaaaaaaa agagatgttc      120
aatcgtttta acaaattcca agctgctgtc gctttggccc tactctctcg cggcgctctc      180
ggtgactctt acaccaatag cacctcctcc gcagacttga gttctatcac ttccgtctcg      240
tcagctagtg caagtgccac cgcttccgac tcactttctt ccagtgacgg taccgtttat      300
ttgccatcca caacaattag cggtgatctc acagttactg gtaaagtaat tgcaaccgag      360
gccgtggaag tcgctgccgg tggtaagttg actttacttg acggtgaaaa atacgtcttc      420
```
tcatctgatc                                                              430

<210> SEQ ID NO 3
<211> LENGTH: 117
<212> TYPE: PRT
<213> ORGANISM: Saccharomyces cerevisiae
<220> FEATURE:
<221> NAME/KEY: PEPTIDE
<222> LOCATION: (1)..(117)
<223> OTHER INFORMATION: TFP2

<400> SEQUENCE: 3

Met Thr Pro Tyr Ala Val Ala Ile Thr Val Ala Leu Leu Ile Val Thr
1               5                   10                  15

Val Ser Ala Leu Gln Val Asn Asn Ser Cys Val Ala Phe Pro Pro Ser
            20                  25                  30

Asn Leu Arg Gly Lys Asn Gly Asp Gly Thr Asn Glu Gln Tyr Ala Thr
        35                  40                  45

Ala Leu Leu Ser Ile Pro Trp Asn Gly Pro Pro Glu Ser Leu Arg Asp
    50                  55                  60

Ile Asn Leu Ile Glu Leu Glu Pro Gln Val Ala Leu Tyr Leu Leu Glu
65                  70                  75                  80

Asn Tyr Ile Asn His Tyr Tyr Asn Thr Thr Arg Asp Asn Lys Cys Pro
                85                  90                  95

Asn Asn His Tyr Leu Met Gly Gly Gln Leu Gly Ser Ser Ser Asp Asn
            100                 105                 110

Arg Ser Leu Asn Asp
        115

<210> SEQ ID NO 4
<211> LENGTH: 424
<212> TYPE: DNA
<213> ORGANISM: Saccharomyces cerevisiae
<220> FEATURE:
<221> NAME/KEY: gene
<222> LOCATION: (1)..(424)
<223> OTHER INFORMATION: TFP2

<400> SEQUENCE: 4
gatctcattg gattcaagag aaagaaactc tatactggcg ccaaattagc agtgtcaaat       60
ttcgaaaagg tgatgacgcc ctatgcagta gcaattaccg tggccttact aattgtaaca      120
gtgagcgcac tccaggtcaa caattcatgt gtcgcttttc cgccatcaaa tctcagaggc      180
aaaaatggag acggtactaa tgaacagtat gcaactgcac tactttctat tccctggaat      240
ggacctcctg agtcattgag ggatattaat cttattgaac tcgaaccgca agttgcactc      300
tatttgctcg aaaattatat taaccattac tacaacacca caagagacaa taagtgccct      360
aataaccact acctaatggg agggcagttg ggtagctcat cggataatag gagtttgaac      420
gatc                                                                   424

<210> SEQ ID NO 5
<211> LENGTH: 104
<212> TYPE: PRT
<213> ORGANISM: Saccharomyces cerevisiae
<220> FEATURE:
<221> NAME/KEY: PEPTIDE
<222> LOCATION: (1)..(104)
<223> OTHER INFORMATION: TFP3

<400> SEQUENCE: 5

Met Gln Phe Lys Asn Val Ala Leu Ala Ala Ser Val Ala Ala Leu Ser

```
                1               5                      10                      15
Ala Thr Ala Ser Ala Glu Gly Tyr Thr Pro Gly Glu Pro Trp Ser Thr
                    20                      25                      30

Leu Thr Pro Thr Gly Ser Ile Ser Cys Gly Ala Ala Glu Tyr Thr Thr
                35                      40                      45

Thr Phe Gly Ile Ala Val Gln Ala Ile Thr Ser Ser Lys Ala Lys Arg
            50                      55                      60

Asp Val Ile Ser Gln Ile Gly Asp Gly Gln Val Gln Ala Thr Ser Ala
65                      70                      75                      80

Ala Thr Ala Gln Ala Thr Asp Ser Gln Ala Gln Ala Thr Thr Thr Ala
                    85                      90                      95

Thr Pro Thr Ser Ser Glu Lys Ile
                100

<210> SEQ ID NO 6
<211> LENGTH: 642
<212> TYPE: DNA
<213> ORGANISM: Saccharomyces cerevisiae
<220> FEATURE:
<221> NAME/KEY: gene
<222> LOCATION: (1)..(642)
<223> OTHER INFORMATION: TFP3

<400> SEQUENCE: 6
gatcccgcct agcccttcca gctttcttt tccccttttt gctacggtcg agacacggtc      60
gcccaaaaga acgggtcag cgtgtactgc gccaaaaaaa ttcgcgccga tttaagctaa     120
acgtccacaa acaaaaacaa aaataagaaa taggttgaca gtgggtgaaa aattctcgaa     180
ggtttcatct ccaaacagtc agtatataag tattcgggaa agagagccaa tctatcttgt     240
ggtgggtcta tcttaacctt ctctttttgg cagtagtaat tgtaaatcaa gacacataaa     300
actatttcac tcgctaaact acatctaaa atgcaattca aaaacgtcgc cctagctgcc      360
tccgttgctg ctctatccgc cactgcttct gctgaaggtt acactccagg tgaaccatgg     420
tccaccttaa ccccaaccgg ctccatctct tgtggtgctg ccgaatacac taccaccttt     480
ggtattgctg ttcaagctat tacctcttca aaagctaaga gagacgttat ctctcaaatt     540
ggtgacggtc aagtccaagc cacttctgct gctactgctc aagccaccga tagtcaagcc     600
caagctacta ctaccgctac cccaaccagc tccgaaaaga tc                       642

<210> SEQ ID NO 7
<211> LENGTH: 50
<212> TYPE: PRT
<213> ORGANISM: Hansenula polymorpha
<220> FEATURE:
<221> NAME/KEY: PEPTIDE
<222> LOCATION: (1)..(50)
<223> OTHER INFORMATION: TFP4

<400> SEQUENCE: 7

Met Arg Phe Ala Glu Phe Leu Val Val Phe Ala Thr Leu Gly Gly Gly
1               5                   10                  15

Met Ala Ala Pro Val Glu Ser Leu Ala Gly Thr Gln Tyr Leu Val
                20                  25                  30

Gln Met Lys Glu Arg Phe Thr Thr Glu Lys Leu Cys Ala Leu Asp Asp
            35                  40                  45

Lys Ile
    50

<210> SEQ ID NO 8
```

```
<211> LENGTH: 179
<212> TYPE: DNA
<213> ORGANISM: Hansenula polymorpha
<220> FEATURE:
<221> NAME/KEY: gene
<222> LOCATION: (1)..(179)
<223> OTHER INFORMATION: TFP4

<400> SEQUENCE: 8
gatccgcttt ttattgcttt gctttgctaa tgagatttgc agaattcttg gtggtatttg      60
ccacgttagg cgggggatg gctgcaccgg ttgagtctct ggccgggacc caacggtatc     120
tggtgcaaat gaaggagcgg ttcaccacag agaagctgtg tgctttggac gacaagatc    179

<210> SEQ ID NO 9
<211> LENGTH: 71
<212> TYPE: PRT
<213> ORGANISM: Saccharomyces cerevisiae
<220> FEATURE:
<221> NAME/KEY: PEPTIDE
<222> LOCATION: (1)..(71)
<223> OTHER INFORMATION: TFP1-3

<400> SEQUENCE: 9

Met Phe Asn Arg Phe Asn Lys Phe Gln Ala Ala Val Ala Leu Ala Leu
1               5                   10                  15

Leu Ser Arg Gly Ala Leu Gly Asp Ser Tyr Thr Asn Ser Thr Ser Ser
            20                  25                  30

Ala Asp Leu Ser Ser Ile Thr Ser Val Ser Ala Ser Ala Ser Ala
        35                  40                  45

Thr Ala Ser Asp Ser Leu Ser Ser Ser Asp Gly Thr Val Tyr Leu Pro
    50                  55                  60

Ser Thr Thr Ile Ser Gly Asp
65                  70

<210> SEQ ID NO 10
<211> LENGTH: 329
<212> TYPE: DNA
<213> ORGANISM: Saccharomyces cerevisiae
<220> FEATURE:
<221> NAME/KEY: gene
<222> LOCATION: (1)..(329)
<223> OTHER INFORMATION: TFP1-4

<400> SEQUENCE: 10
ggatccatgt tcaatcgttt taacaaattc caagctgctg tcgctttggc cctactctct      60
cgcggcgctc tcggtgactc ttacaccaat agcacctcct ccgcagactt gagttctatc    120
acttccgtct cgtcagctag tgcaagtgcc accgcttccg actcactttc ttccagtgac    180
ggtaccgttt atttgccatc cacaacaatt agcggtgatc tcacagttac tggtaaagta    240
attgcaaccg aggccgtgga agtcgctgcc ggtggtaagt tgactttact tgacggtgaa    300
aaatacgtct tctcatctga tcctctaga                                      329

<210> SEQ ID NO 11
<211> LENGTH: 35
<212> TYPE: DNA
<213> ORGANISM: Artificial Sequence
<220> FEATURE:
<223> OTHER INFORMATION: JH97(Sfi-HSA-forward primer)

<400> SEQUENCE: 11
ccggccatta cggccgtgat gcacacaaga gtgag                                35
```

```
<210> SEQ ID NO 12
<211> LENGTH: 29
<212> TYPE: DNA
<213> ORGANISM: Artificial Sequence
<220> FEATURE:
<223> OTHER INFORMATION: JH119(Sfi-HSA-reverse primer)

<400> SEQUENCE: 12
ccggccgagg cggcctaagc ctaaggcag                               29

<210> SEQ ID NO 13
<211> LENGTH: 50
<212> TYPE: DNA
<213> ORGANISM: Artificial Sequence
<220> FEATURE:
<223> OTHER INFORMATION: JH99(Sfi-INV-forward primer)

<400> SEQUENCE: 13
gggcggccgc ctcggcccta gataaaaggt caatgacaaa cgaaactagc         50

<210> SEQ ID NO 14
<211> LENGTH: 32
<212> TYPE: DNA
<213> ORGANISM: Artificial Sequence
<220> FEATURE:
<223> OTHER INFORMATION: JH100(SalI-INV-reverse primer)

<400> SEQUENCE: 14
ccgtcgactt actattttac ttcccttact tg                            32

<210> SEQ ID NO 15
<211> LENGTH: 37
<212> TYPE: DNA
<213> ORGANISM: Artificial Sequence
<220> FEATURE:
<223> OTHER INFORMATION: JH106(Sfi-IL2-forward primer)

<400> SEQUENCE: 15
gcggccatta cggccgtgca cctacttcaa gttctac                       37

<210> SEQ ID NO 16
<211> LENGTH: 37
<212> TYPE: DNA
<213> ORGANISM: Artificial Sequence
<220> FEATURE:
<223> OTHER INFORMATION: JH107(Sfi-IL2-reverse primer)

<400> SEQUENCE: 16
gcggccatta cggccgtgca cctacttcaa gttctac                       37

<210> SEQ ID NO 17
<211> LENGTH: 26
<212> TYPE: DNA
<213> ORGANISM: Artificial Sequence
<220> FEATURE:
<223> OTHER INFORMATION: JH120(BamHI-IL2-1-forward primer)

<400> SEQUENCE: 17
cgggatccgc acctacttca agttct                                   26

<210> SEQ ID NO 18
<211> LENGTH: 27
<212> TYPE: DNA
<213> ORGANISM: Artificial Sequence
<220> FEATURE:
<223> OTHER INFORMATION: JH121(BamHI-IL2-2-forward primer)

<400> SEQUENCE: 18
```

```
cgggatcctg cacctacttc aagttct                                          27
```

<210> SEQ ID NO 19
<211> LENGTH: 28
<212> TYPE: DNA
<213> ORGANISM: Artificial Sequence
<220> FEATURE:
<223> OTHER INFORMATION: JH122(BamHI-IL2-3-forward primer)

<400> SEQUENCE: 19

```
cgggatcctt gcacctactt caagttct                                         28
```

<210> SEQ ID NO 20
<211> LENGTH: 22
<212> TYPE: DNA
<213> ORGANISM: Artificial Sequence
<220> FEATURE:
<223> OTHER INFORMATION: JH123(INV-1-reverse primer)

<400> SEQUENCE: 20

```
ccattgaagg aaccaacaaa at                                               22
```

<210> SEQ ID NO 21
<211> LENGTH: 22
<212> TYPE: DNA
<213> ORGANISM: Artificial Sequence
<220> FEATURE:
<223> OTHER INFORMATION: JH124(INV-forward primer)

<400> SEQUENCE: 21

```
attttgttgg ttccttcaat gg                                               22
```

<210> SEQ ID NO 22
<211> LENGTH: 29
<212> TYPE: DNA
<213> ORGANISM: Artificial Sequence
<220> FEATURE:
<223> OTHER INFORMATION: JH95(INV-2-reverse primer)

<400> SEQUENCE: 22

```
ggctcgagct attttacttc ccttacttg                                        29
```

<210> SEQ ID NO 23
<211> LENGTH: 23
<212> TYPE: DNA
<213> ORGANISM: Artificial Sequence
<220> FEATURE:
<223> OTHER INFORMATION: JH132(SacI-GAL-forward primer)

<400> SEQUENCE: 23

```
gggagctcat cgcttcgctg att                                              23
```

<210> SEQ ID NO 24
<211> LENGTH: 27
<212> TYPE: DNA
<213> ORGANISM: Artificial Sequence
<220> FEATURE:
<223> OTHER INFORMATION: JH137(IL-2-Term-reverse primer)

<400> SEQUENCE: 24

```
ccgtcgactt aagttagtgt tgagatg                                          27
```

<210> SEQ ID NO 25
<211> LENGTH: 47
<212> TYPE: DNA
<213> ORGANISM: Artificial Sequence

```
-continued

<220> FEATURE:
<223> OTHER INFORMATION: HY22(TFP1-LDKR-reverse primer)

<400> SEQUENCE: 25
gaacttgaag taggtgccct tttatctaga ggatcagatg agaagac          47

<210> SEQ ID NO 26
<211> LENGTH: 46
<212> TYPE: DNA
<213> ORGANISM: Artificial Sequence
<220> FEATURE:
<223> OTHER INFORMATION: HY23(TFP1-LDKR-forward primer)

<400> SEQUENCE: 26
tcttctcatc tgatcctcta gataaaaggg cacctacttc aagttc           46

<210> SEQ ID NO 27
<211> LENGTH: 46
<212> TYPE: DNA
<213> ORGANISM: Artificial Sequence
<220> FEATURE:
<223> OTHER INFORMATION: HY20(TFP2-LDKR-reverse primer)

<400> SEQUENCE: 27
gaacttgaag taggtgccct tttatctaga ggatcgttca aactcc           46

<210> SEQ ID NO 28
<211> LENGTH: 46
<212> TYPE: DNA
<213> ORGANISM: Artificial Sequence
<220> FEATURE:
<223> OTHER INFORMATION: HY21(TFP2-LDKR-forward primer)

<400> SEQUENCE: 28
ggagtttgaa cgatcctcta gataaaaggg cacctacttc aagttc           46

<210> SEQ ID NO 29
<211> LENGTH: 47
<212> TYPE: DNA
<213> ORGANISM: Artificial Sequence
<220> FEATURE:
<223> OTHER INFORMATION: HY24(TFP4-LDKR-reverse primer)

<400> SEQUENCE: 29
gaacttgaag taggtgccct tttatcaagg atcttgtcgt ccaaagc          47

<210> SEQ ID NO 30
<211> LENGTH: 47
<212> TYPE: DNA
<213> ORGANISM: Artificial Sequence
<220> FEATURE:
<223> OTHER INFORMATION: HY25(TFP4-LDKR-forward primer)

<400> SEQUENCE: 30
gctttggacg acaagatcct tgataaaagg gcacctactt caagttc          47

<210> SEQ ID NO 31
<211> LENGTH: 27
<212> TYPE: DNA
<213> ORGANISM: Artificial Sequence
<220> FEATURE:
<223> OTHER INFORMATION: JH143(XbaI-TFP1-d-reverse primer)

<400> SEQUENCE: 31
cctctagaat caccgctaat tgttgtg                                27
```

<210> SEQ ID NO 32
<211> LENGTH: 27
<212> TYPE: DNA
<213> ORGANISM: Artificial Sequence
<220> FEATURE:
<223> OTHER INFORMATION: JH142(XbaI-TFP1-c-reverse primer)

<400> SEQUENCE: 32
cctctagagg tgctattggt gtaagag       27

<210> SEQ ID NO 33
<211> LENGTH: 27
<212> TYPE: DNA
<213> ORGANISM: Artificial Sequence
<220> FEATURE:
<223> OTHER INFORMATION: JH141(XbaI-TFP1-b-reverse primer)

<400> SEQUENCE: 33
cctctagaac cgagagcgcc gcgagag       27

<210> SEQ ID NO 34
<211> LENGTH: 25
<212> TYPE: DNA
<213> ORGANISM: Artificial Sequence
<220> FEATURE:
<223> OTHER INFORMATION: JH140(SpeI-XbaI-LDKR-forward primer

<400> SEQUENCE: 34
ggactagtct agataaaagg gcacc       25

<210> SEQ ID NO 35
<211> LENGTH: 42
<212> TYPE: DNA
<213> ORGANISM: Artificial Sequence
<220> FEATURE:
<223> OTHER INFORMATION: HY38(TFP1-UTR-forward primer)

<400> SEQUENCE: 35 gaattttga aaattcaagg atccatgttc aatcgtttta ac       42

<210> SEQ ID NO 36
<211> LENGTH: 33
<212> TYPE: DNA
<213> ORGANISM: Artificial Sequence
<220> FEATURE:
<223> OTHER INFORMATION: JH144(GCSF-forward primer)

<400> SEQUENCE: 36
cctctagata aaaggacccc cctgggccct gcc       33

<210> SEQ ID NO 37
<211> LENGTH: 28
<212> TYPE: DNA
<213> ORGANISM: Artificial Sequence
<220> FEATURE:
<223> OTHER INFORMATION: JH145(GCSF-reverse primer)

<400> SEQUENCE: 37
ggcagctgga tgtattttac atggggag       28

<210> SEQ ID NO 38
<211> LENGTH: 43
<212> TYPE: DNA
<213> ORGANISM: Artificial Sequence
<220> FEATURE:
<223> OTHER INFORMATION: HY17(TFP3-LDKR-reverse primer)

<400> SEQUENCE: 38

```
gaacttgaag taggtgccct tttatcaagg atcttttcgg agc                        43
```

<210> SEQ ID NO 39
<211> LENGTH: 43
<212> TYPE: DNA
<213> ORGANISM: Artificial Sequence
<220> FEATURE:
<223> OTHER INFORMATION: HY18(TFP3-LDKR-forward primer)

<400> SEQUENCE: 39

```
gctccgaaaa gatccttgat aaagggcac ctacttcaag ttc                         43
```

<210> SEQ ID NO 40
<211> LENGTH: 134
<212> TYPE: PRT
<213> ORGANISM: Saccharomyces cerevisiae
<220> FEATURE:
<221> NAME/KEY: PEPTIDE
<222> LOCATION: (1)..(134)
<223> OTHER INFORMATION: TFP3-1-1

<400> SEQUENCE: 40

Met Gln Phe Lys Asn Val Ala Leu Ala Ala Ser Val Ala Ala Leu Ser
1               5                   10                  15

Ala Thr Ala Ser Ala Glu Gly Tyr Thr Pro Gly Glu Pro Trp Ser Thr
            20                  25                  30

Leu Thr Pro Thr Gly Ser Ile Ser Cys Gly Ala Ala Glu Tyr Thr Thr
        35                  40                  45

Thr Phe Gly Ile Ala Val Gln Ala Ile Thr Ser Ser Lys Ala Lys Arg
    50                  55                  60

Asp Val Ile Ser Gln Ile Gly Asp Gly Gln Val Gln Ala Thr Ser Ala
65                  70                  75                  80

Ala Thr Ala Gln Ala Thr Asp Ser Gln Ala Gln Ala Thr Thr Thr Ala
                85                  90                  95

Thr Pro Thr Ser Ser Glu Lys Ile Ser Ser Ser Ala Ser Lys Thr Ser
            100                 105                 110

Thr Asn Ala Thr Ser Ser Ser Cys Ala Thr Pro Ser Leu Lys Asp Ser
        115                 120                 125

Ser Cys Lys Asn Ser Gly
    130

<210> SEQ ID NO 41
<211> LENGTH: 402
<212> TYPE: DNA
<213> ORGANISM: Saccharomyces cerevisiae
<220> FEATURE:
<221> NAME/KEY: gene
<222> LOCATION: (1)..(402)
<223> OTHER INFORMATION: TFP3-1-1

<400> SEQUENCE: 41

```
atgcaattca aaacgtcgc cctagctgcc tccgttgctg ctctatccgc cactgcttct        60
gctgaaggtt acactccagg tgaaccatgg tccaccttaa ccccaaccgg ctccatctct      120
tgtggtgctg ccgaatacac taccaccttt ggtattgctg ttcaagctat acctcttca      180
aaagctaaga gagacgttat ctctcaaatt ggtgacggtc aagtccaagc cacttctgct      240
gctactgctc aagccaccga tagtcaagcc caagctacta ctaccgctac cccaaccagc      300
tccgaaaaga tctcttcctc tgcatctaaa acatcctact atgccacatc atcttcttgt      360
gccactccat ctttgaaaga tagctcatgt aagaattctg gt                         402
```

```
<210> SEQ ID NO 42
<211> LENGTH: 143
<212> TYPE: PRT
<213> ORGANISM: Saccharomyces cerevisiae
<220> FEATURE:
<221> NAME/KEY: PEPTIDE
<222> LOCATION: (1)..(143)
<223> OTHER INFORMATION: TFP3-1-2

<400> SEQUENCE: 42

Met Gln Phe Lys Asn Val Ala Leu Ala Ala Ser Val Ala Ala Leu Ser
1               5                   10                  15

Ala Thr Ala Ser Ala Glu Gly Tyr Thr Pro Gly Glu Pro Trp Ser Thr
            20                  25                  30

Leu Thr Pro Thr Gly Ser Ile Ser Cys Gly Ala Ala Glu Tyr Thr Thr
        35                  40                  45

Thr Phe Gly Ile Ala Val Gln Ala Ile Thr Ser Ser Lys Ala Lys Arg
    50                  55                  60

Asp Val Ile Ser Gln Ile Gly Asp Gly Gln Val Gln Ala Thr Ser Ala
65                  70                  75                  80

Ala Thr Ala Gln Ala Thr Asp Ser Gln Ala Gln Ala Thr Thr Thr Ala
                85                  90                  95

Thr Pro Thr Ser Ser Glu Lys Ile Ser Ser Ser Ala Ser Lys Thr Ser
            100                 105                 110

Thr Asn Ala Thr Ser Ser Ser Cys Ala Thr Pro Ser Leu Lys Asp Ser
        115                 120                 125

Ser Cys Lys Asn Ser Gly Thr Leu Glu Leu Thr Leu Lys Asp Gly
    130                 135                 140

<210> SEQ ID NO 43
<211> LENGTH: 429
<212> TYPE: DNA
<213> ORGANISM: Saccharomyces cerevisiae
<220> FEATURE:
<221> NAME/KEY: gene
<222> LOCATION: (1)..(429)
<223> OTHER INFORMATION: TFP3-1-2

<400> SEQUENCE: 43
atgcaattca aaacgtcgc cctagctgcc tccgttgctg ctctatccgc cactgcttct      60
gctgaaggtt acactccagg tgaaccatgg tccaccttaa ccccaaccgg ctccatctct    120
tgtggtgctg ccgaatacac taccaccttt ggtattgctg ttcaagctat tacctcttca    180
aaagctaaga gagacgttat ctctcaaatt ggtgacggtc aagtccaagc cacttctgct    240
gctactgctc aagccaccga tagtcaagcc aagctactac taccgctac cccaaccagc    300 tccgaaaaga tctcttcctc tgcatctaaa acatctacta tgccacatc atcttcttgt    360 gccactccat ctttgaaaga tagctcatgt aagaattctg gtaccttaga attgaccttg    420
aaggacggt                                                           429

<210> SEQ ID NO 44
<211> LENGTH: 25
<212> TYPE: DNA
<213> ORGANISM: Artificial Sequence
<220> FEATURE:
<223> OTHER INFORMATION: BglII-GAP-forward primer

<400> SEQUENCE: 44
gcaagatctg gatcctttt tgtag                                           25
```

```
<210> SEQ ID NO 45
<211> LENGTH: 26
<212> TYPE: DNA
<213> ORGANISM: Artificial Sequence
<220> FEATURE:
<223> OTHER INFORMATION: GAP-EcoRI-reverse primer

<400> SEQUENCE: 45
aagaattctt gatagttgtt caattg                                          26
```